US008545378B2

(12) United States Patent
Peterchev

(10) Patent No.: US 8,545,378 B2
(45) Date of Patent: Oct. 1, 2013

(54) SYSTEMS AND METHODS FOR INDUCING ELECTRIC FIELD PULSES IN A BODY ORGAN

(75) Inventor: Angel Vladimirov Peterchev, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1073 days.

(21) Appl. No.: 12/304,971

(22) PCT Filed: May 31, 2007

(86) PCT No.: PCT/US2007/012825
§ 371 (c)(1),
(2), (4) Date: Jul. 10, 2009

(87) PCT Pub. No.: WO2007/145838
PCT Pub. Date: Dec. 21, 2007

(65) Prior Publication Data
US 2010/0069704 A1 Mar. 18, 2010

Related U.S. Application Data

(63) Continuation-in-part of application No. 11/729,517, filed on Mar. 28, 2007, now Pat. No. 7,753,836.

(60) Provisional application No. 60/814,277, filed on Jun. 15, 2006, provisional application No. 60/905,561, filed on Mar. 7, 2007.

(51) Int. Cl.
A61N 1/00 (2006.01)

(52) U.S. Cl.
USPC .......................................................... 600/14

(58) Field of Classification Search
USPC ........................................................ 600/9–15
See application file for complete search history.

(56) References Cited

U.S. PATENT DOCUMENTS

| 4,914,540 A | 4/1990 | Tabata et al. |
| 5,030,196 A | 7/1991 | Inoue |
| 5,327,854 A | 7/1994 | Smith et al. |
| 5,707,334 A | 1/1998 | Young |
| 5,769,778 A | 6/1998 | Abrams et al. |
| 5,813,970 A | 9/1998 | Abrams et al. |
| 5,833,600 A | 11/1998 | Young |

(Continued)

FOREIGN PATENT DOCUMENTS

EP 1894600 A1 3/2008

OTHER PUBLICATIONS

ABB Switzerland Ltd. (2005). HiPak™ GBT Modules with SPT Chips. From http://www.abb.com/semiconductors.

(Continued)

Primary Examiner — John Lacyk
(74) Attorney, Agent, or Firm — Mark A. Catan; Miles & Stockbridge P.C.

(57) ABSTRACT

Systems and methods for providing controllable pulse parameter magnetic stimulation are described. One aspect is directed to a magnetic stimulation system for inducing approximately rectangular electric field pulses in a body organ, comprising an electrical energy storage device, a stimulating coil, and a switching means for electrically coupling said electrical energy storage device to said stimulating coil to produce current pulses in said stimulating coil which generates, in response to the current pulses, magnetic field pulses that can induce approximately rectangular electric field pulses in the body organ.

47 Claims, 18 Drawing Sheets

(56) References Cited

U.S. PATENT DOCUMENTS

| | | | |
|---|---|---|---|
| 6,117,066 | A | 9/2000 | Abrams et al. |
| 6,123,658 | A | 9/2000 | Schweighofer et al. |
| 6,179,770 | B1 | 1/2001 | Mould |
| 6,198,958 | B1 | 3/2001 | Ives et al. |
| 6,402,678 | B1 | 6/2002 | Fischell et al. |
| 6,551,233 | B2 | 4/2003 | Perreault et al. |
| 6,572,528 | B2 | 6/2003 | Rohan et al. |
| 6,591,138 | B1 | 7/2003 | Fischell et al. |
| 6,899,667 | B2 | 5/2005 | Becker et al. |
| 6,926,660 | B2 | 8/2005 | Miller |
| 6,978,179 | B1 | 12/2005 | Flagg et al. |
| 6,983,184 | B2 | 1/2006 | Price |
| 7,069,067 | B2 | 6/2006 | Kuth |
| 7,087,008 | B2 | 8/2006 | Fox et al. |
| 7,104,947 | B2 | 9/2006 | Riehl |
| 7,130,203 | B2 | 10/2006 | Mbaye |
| 7,153,256 | B2 | 12/2006 | Riehl et al. |
| 7,160,240 | B2 | 1/2007 | Frimerman |
| 7,231,254 | B2 | 6/2007 | DiLorenzo |
| 7,276,020 | B2 | 10/2007 | Becker et al. |
| 7,277,758 | B2 | 10/2007 | DiLorenzo |
| 7,282,021 | B2 | 10/2007 | Rohan et al. |
| 7,294,101 | B2 | 11/2007 | Fischell et al. |
| 7,320,664 | B2 | 1/2008 | Riehl et al. |
| 7,407,478 | B2 | 8/2008 | Zangen et al. |
| 2005/0288744 | A1 | 12/2005 | Pilla et al. |
| 2006/0052657 | A9 | 3/2006 | Zabara |
| 2007/0203390 | A1 | 8/2007 | Rohan |
| 2007/0282388 | A1 | 12/2007 | Sandyk |
| 2007/0293916 | A1 | 12/2007 | Peterchev |
| 2008/0121232 | A1 | 5/2008 | Cewers |

OTHER PUBLICATIONS

ABB Switzerland Ltd. (2005). IGBT Module 5SNA0900E450100. From http://www.abb.com/semiconductors.

ABB Switzerland Ltd. (2005). Reverse Conducting Integrated Gate-Commutated Thyristor 5SHX26L4510. From http://www.abb.com.

Amassian V. E., Cracco, R. Q., Maccabee, P. J, Cracco, J. B., Rudell, A., and Eberle, L. (1989). Suppression of visual perception by magnetic coil stimulation of human occipital cortex. *Electroencephalogr Clin Neurophysiol*, 74(6), 458-462.

Antal, A., Kincses, T. Z., Nitsche, M. A., Bartfai O, Demmer I., Sommer, M., and Paulus, W. (2002). Pulse configuration-dependent effects of repetitive transcranial magnetic stimulation on visual perception. *Neuroreport*, 13(17), 2229-2233.

Arai, N., Okabe, S., Furubayashi, T., Terao Y., Yuasa, K., and Ugawa, Y. (2005). Comparison between short train, monophasic and biphasic repetitive transcranial magnetic stimuation (rTMS) of the human motor cortex. *Clin Neurophysiol*, 116(3), 605-613.

Berardelli, A., Inghilleri, M., Rothwell, J. C., Romeo, S., Curra, A., Gilio, F., Modugno N., and Manfredi, M. (1998). Facilitation of muscle evoked responses after repetitive cortical stimulation in man. *Exp Brain Res*, 122(1), 7984.

Berman, R. M., Sackeim, H. A., Truesdale, M. D., Luber, B., Schroeder, C., and Lisanby, S. H. (2005). Focal electrically-administered seizure therapy (feast): Nonhuman primate studies of a novel form of focal brain stimulation. J ECT, 21 57.

Brasil-Neto, J. P., Cohen, L. G., Panizza, M., Nilsson, J., Roth, B. J., and Hallett, M. (1992). Optimal focal transcranial magnetic activation of the human motor cortex: effects of coil orientation, shape of the induced current pulse, and stimulus intensity. *J Clin Neurophysiol*, 9(1), 132-136.

Cadwell, J. (1991). Optimizing magnetic stimulator design. *Electroencephalogr Clin Neurophysiol Suppl*. 43, 238-248.

Chen, R., Classen, J., Gerloff, C., Celnik, P., Wassermann, E. M., Hallet, M., and Cohen, L. G. (1997). Depression of motor cortex excitability by low-frequency transcranial magnetic stimulation. *Neurology*, 48(5), 1398-1403.

Corthout, E., Barker, A. T., and Cowey, A., "Transcranial magnetic stimulation: Which part of the current waveform causes the stimulation?" *Exp Brain Res*, vol. 141, No. 1, pp. 128-132, 2001.

Curra, A., Modugno, N., Inghilleri, M., Manfredi, M., Hallett, M., and Berardelli, A. (2002). Transcranial magnetic stimulation techniques in clinical investigation. Neurology, 59(12), 1851-1859.

Davey, K. and Epstein, C. M. (2000). Magnetic stimulation coil and circuit design. IEEE Trans Biomed Eng, 47(11), 1493-1499.

Di Lazzaro, V., Oliviero, A., Mazzone, P., Pilato, F., Saturno, E., Dileone, M., and Tonali, P. A. (2003). Generation of I waves in the human: spinal recordings. Suppl Clin Neurophysiol, 56, 143-152.

Di Lazzaro, V., Oliviero, A., Pilato, F., Saturno, E., Dileone, M., Mazzone, P., Insola, A., Tonali, P. A., and Rothwell, J. C., (2004). The physiological basis of transcranial motor cortex stimulation in conscious humans. Clin Neurophysiol, 112), 255-266.

Digitimer Limited. (2005). MultiPulse Stimulator D185—Mk.II. From http://www.digitimer.com.

Dubach, M. F., Tongen, V. C., and Bowden, D. M. (1985). Techniques for improving stereotaxic accuracy in *Macaca fascicularis*. *J Neurosci Methods*, 13(2), 163-169.

Epstein, C. M., Schwartzberg, D. G., Davey, K. R., and Sudderth, D. B. (1990). Localizing the site of magnetic brain stimulation in humans. *Neurology*, 40(4), 666-670.

Esser, S. K., Hill, S. L., and Tononi, G. (2005). Modeling the effects of transcranial magnetic stimulation on cortical circuits. *J Neurophysiol*, 94(1), 622-639.

Fitzgerald, P. B., Benitez, J., de Castella, A., Daskalakis, Z. J., Brown, T. L., and Kulkarni, J. (2006). A randomized, controlled trial of sequential bilateral repetitive transcranial magnetic stimulation for treatment-resistant depression. *Am J Psychiatry*, 163(1), 38-94.

General Atomics Electronic Systems Inc. (1999). Capacitor Specification. Model No. 310DM475. From http://www.gaep.com/capacitors.html.

General Atomics Electronic Systems Inc. (2003). Series DP: Drawn Metal Can High Voltage Capacitors. From http://www.gaep.com/series-dp-capacitors.html.

Gershon, A. A., Dannon, P. N., and Grunhaus, L. (2003). Transcranial magnetic stimulation in the treatment of depression. Am J Psychiatry, 160(5), 835-845.

Huang, Y, Z., Edwards, M. J., Rounis, E., Bhatia, K. P., and Rothwell, J. C, (2005). Theta burst stimulation of the human motor cortex. Neuron, 42), 201-206.

Jalinous, R. Technical and practical aspects of magnetic nerve stimulation. J Clin Neurophysiol, vol. 8, No. 1, pp. 10-25, 1991.

Kammer, T., Beck, S., Thielscher, A., Laubis-Herrmann, U., and Topka, H. (2001). Motor thresholds in humans: a transcranial magnetic stimulation study comparing different pulse waveforms, current directions and stimulator types. Clin Neurophysiol, 112(2), 250-258.

Kolachana, B. S., Saunders, R. C., and Weinberger, D. R. (1995). Augmentation of prefrontal cortical monoaminergic activity inhibits dopamine release in the caudate nucleus: an in vivo neurochemical assessment in the rhesus monkey. Neuroscience, 69(3), 859-868.

Lisanby, S. H, Guthman, D., Luber, B., Schroeder, C., and Sackeim, H. A. (2001). Sham TMS: intracerebral measurement of the induced electrical field and the induction of motor-evoked potentials. Biol Psychiatry, 49(5), 460-463.

Lisanby, S. H., Wassermann, E. M., Ziemann, U., Luber, B., Finck, D., Osman, M., Dichter, G., and Sackeim, H. A. (1997). Motor evoked potentials to paired transcranial magnetic stimulation (TMS) in the alert and sedated rhesus monkey. Electroencephalogr Clin Neurophysiol, 103, 151.

Martin, R. F. and Bowden, D. M. (1996). A stereotaxic template atlas of the macaque brain for digital imaging and quantitative neuroanatomy. Neuroimage, 4(2), 119-150.

McCreery, D. B., Agnew, W. F., Yuen, T. G., and Bullara, L. (1990). Charge density and charge per phase as cofactors in neural injury induced by electrical stimulation. IEEE Trans Biomed Eng, 37(10),996-1001.

Merton, P. A. and Morton, H. B. (1980). Stimulation of the cerebral cortex in the intact human subject. Nature, 285(5762), 227.

Morales, O.G., Sackeim, H. A., Berman, R. M., and Lisanby, S. H. Magnetic seizure therapy: development of a novel intervention for treatment resistant depression. Clin Neurosci Res, vol. 4, pp. 59-70, 2004.

Nahm, F. K., Dale, A. M., Albright, T. D., and Amaral, D. G. (1994). In vivo microelectrode localization in the brain of the alert monkey: a combined radiographic and magnetic resonance imaging approach. Exp Brain Res, 98(3), 401-411.

National Instruments Corp. (2005). NI PCI-7041/6040E. From http://www.ni.com.

National Instruments Corp. (2005). R Series Intelligent DAQ with Onboard Processing. From http://www.ni.com.

Orth, M. and Rothwell, J. C. (2004). The cortical silent period: intrinsic variability and relation to the waveform of the transcranial magnetic stimulation pulse. Clin Neurophysiol, 115(5), 1076-1082.

Panizza, M., Nilsson, J., Roth, B. J., Basser, P. J., and Hallett, M. (1992). Relevance of stimulus duration for activation of motor and sensory fibers: implications for the study of H-reflexes and magnetic stimulation. Electroencephalogr Clin Neurophysiol, 85(1), 22-29.

Pascual-Leone, A., Tormos, J. M., Keenan, J., Tarazona, F., Canete, C., and Catala, M. D. (1998). Study and modulation of human cortical excitability with transcranial magnetic stimulation. J Clin Neurophysiol, 15(4), 333-343.

Pudenz, R. H., Bullara, L. A., Jacques, S., and Hambrecht, F. T. (1975). Electrical stimulation of the brain. III. The neural damage model. Surg Neurol, 4(4), 389-400.

Roth, B. J. and Basser, P. J. (1990). A model of the stimulation of a nerve fiber by electromagnetic induction. IEEE Transactions on Biomedical Engineering, vol. 37, No. 6, Jun. 1990.

Roth, B. J., Cohen, L. G., and Hallett, M. (1991). The electric field induced during magnetic stimulation. Electroencephalogr Clin Neurophysiol Suppl, 43, 268-278.

Sackeim, H. A., Long, J., Luber, B., Moeller, J. R., Prohovnik, I., Devanand, D. P., and Nobler, M. S. (1994). Physical properties and quantification of the ECT stimulus: I. Basic principles. Convulsive Therapy, 10(2):93-123 © 1994 Raven Press, Ltd., New York.

Saunders, R. C., Aigner, T. G., and Frank, J. A. (1990). Magnetic resonance imaging of the rhesus monkey brain: use for stereotactic neurosurgery. Exp Brain Res, 81(2), 443-446.

Saunders, R. C., Kolachana, B. S., and Weinberger, D. R. (1994). Local pharmacological manipulation of extracellular dopamine levels in the dorsolateral prefrontal cortex and caudate nucleus in the rhesus monkey: an in vivo microdialysis study. Exp Brain Res, 98(1), 44-52.

Schroeder, C. E., Mehta, A. D., and Givre, S. J. (1998). A spatiotemporal profile of visual system activation revealed by current source density analysis in the awake macaque. Cereb Cortex, 8(7), 575-592.

Schroeder, C. E., Steinschneider, M., Javitt, D. C., Tenke, C. E., Givre, S. J., Mehta, A. D., Simpson, G. V., Arezzo, J. C., and Vaughan, H. G., Jr. (1995). Localization of ERP generators and identification of underlying neural processes. Electroencephalogr Clin Neurophysiol Suppl, 44, 55-75.

Sommer, M., Lang, N., Tergau, F., and Paulus, W. (2002). Neuronal tissue polarization induced by repetitive transcranial magnetic stimulation? Neuroreport, 13(6), 809-811.

Szabo, J. and Cowan, W. M. (1984). A stereotaxic atlas of the brain of the cynomolgus monkey (*Macaca fascicularis*). J Comp Neurol, 222(2), 265-300.

Taylor, J. L. and Loo, C K. Stimulus waveform influences the efficacy of repetitive transcranial magnetic stimulation. J Affect Disord, vol. 97, pp. 271-276, 2007.

Tings, T., Lang, N., Tergau, F., Paulus, W., and Sommer, M. (2005). Orientation-specific fast rTMS maximizes corticospinal inhibition and facilitation. Exp Brain Res, 164(3), 323-333.

Tofts, P. S. and Branston, N. M. (1991). The measurement of electric field, and the influence of surface charge, in magnetic stimulation. Electroencephalogr Clin, Neurophysiol, 81(3), 238-239.

Walsh, V. and Cowey, A. (2000). Transcranial magnetic stimulation and cognitive neuroscience. Nat Rev Neurosci, 1(1), 73-79.

Wassermann, E. M. and Lisanby, S. H. (2001). Therapeutic application of repetitive transcranial magnetic stimulation: a review. Clin Neurophysiol. 112(8), 1 3671 377.

Weiner, R D. (1980). ECT and seizure threshold: effects of stimulus wave form and electrode placement. Biol Psychiatry, 15(2), 225241.

Weiner, R. D. and Coffey, C. E. (1989). Comparison of Brief-Pulse and Sine Wave ECT Stimuli. Convuls Ther, 5(2), 184185.

Weissman, J. D., Epstein, C. M., and Davey, K. R. (1992). Magnetic brain stimulation and brain size: relevance to animal studies. Electroencephalogr Clin Neurophysiol, 85(3), 21 521 9.

Written Opinion of the International Searching Authority dated Sep. 9, 2008.

European Search Report dated May 29, 2009, European Application No. 07 809261.6.

European Search Report dated Oct. 16, 2009, European Application No. 07 809261.6.

Angel V. Peterchev, Timothy J. Spellman and Sarah H. Lisanby, "cTMS: A novel TMS Device Inducing Near Rectangular Pulses with Controllable Pulse Width", Neuropshychopharmacology, vol. 31, No. 1, ACNP 2006 Annual Meeting, PS130.

A.T. Barker, R. Jalinous, I.L. Freeston, "Non-Invasive Magnetic Stimulation of Human Motor Cortex", The Lancet, May 11, 1985, pp. 1106-1107.

Reza Jalinous, "Principles of magnetic stimulator design", Handbook of Transcranial Magnetic Stimulation, A. Pascual-Leone, N. J. Davey, J. Rothwell, E. M. Wassermann, and B. Arnold, 2002, pp. 30-38.

Jarmo Ruohonen and Risto J. Ilmoniemi, "Basic Physics and Design of Transcranial Magnetic Stimulation Devices and Coils", Magnetic Stimulation in Clinical Neurophysiology, M. Hallett and S. Chokroverty, Eds., $2^{nd}$ ed., Philadelphia, PA: Elsevier Butterworth-Heinemann, 2005, pp. 17-30.

Angel V. Peterchev, Reza Jalinous, and Sarah H. Lisanby, "A Transcranial magnetic Stimulator Inducing Near-Rectangular Pulses With Controllable Pulse Width (cTMS)", IEEE vol. 55, No. 1, Jan. 2008, pp. 257-266.

Soile Komssi, "Electroencephalographic Responses to Transcranial Magnetic Stimulation", University of Helsinki, Report series in Physics, Academic Dissertation, Nov. 27, 2004, pp. 1-47.

P. J. Maccabee, S. S. Nagarajan, V. E. Amassian, D. M. Durand, A. Z. Szabo, A. B. Ahad, R. Q. Cracco, K. S. Lai and L. P. Eberle, "Influence of pulse sequence, polarity and amplitude on magnetic stimulation of human and porcine peripheral nerve", Journal of Physiology (1998), 513.2, pp. 571-585, Accepted after revision Aug. 13, 1998.

A.T. Barker, C.W. Garnham, I.L. Freeston, "Magnetic nerve stimulation: The effect of waveform on efficiency, determinaton of neural membrane time constants and the measurement of stimulator output", Electroencephalogr. Clin. Neurophysiol. Suppl., vol. 43, pp. 227-237, 1991.

International Search Report, dated Sep. 9, 2008, for International Application No. PCT/US07/12825.

Paulus et al., "Transcranial Magnetic Stimulation," *Proceedings of the International Symposium on Transcranial Magnetic Stimulation*, Sep. 30-Oct. 4, 1999, *Electroencephalography and Clinical Neurophysiology*, 1999, Suppl. 51: pp. 8-10.

Myers, A.M., "Improving the Efficiency of Magnetic Stimulation of Nerves," Department of Medical Physics and Clinical Engineering, The University of Sheffield, Feb. 2005, Chapter 8: pp. 114-121.

Extended European Search Report and Search Opinion issued Mar. 13, 2012, in European Patent Application No. 10778324.3.

| PARAMETER | SYMBOL | MONOPHASIC MAGNETIC PULSE | | | BIPHASIC MAGNETIC PULSE | | | | | UNIT |
|---|---|---|---|---|---|---|---|---|---|---|
| | | MAGSTIM 200 | MAGPRO X100 | cTMS1 | MAGSTIM RAPID2 | NEURONETICS 2100 | cTMS2 | cTMS3 | cTMS4 | |
| POSITIVE CAPACITOR VOLTAGE | $V_{C1}$ | 1,316 | 1,506 | 1,506 | 1,076 | 1,645 | 1,645 | 1,645 | 2,800 | V |
| NEGATIVE CAPACITOR VOLTAGE | $-V_{C2}$ | - | - | -602 | - | - | -165 | -411 | -700 | V |
| COIL CURRENT RISE TIME | $t_{RISE}$ | 86 | 70 | 42 | 173* | 100* | 42* | 49* | 31* | μs |
| COIL DISCHARGE TIME CONSTANT | $\tau_{FALL} = L/R$ | 182 | 204 | - | - | - | - | - | - | μs |
| EFFECTIVE PW ** | $PW_{eff}$ | 70 | 60 | 42 | 92 | 54 | 35 | 35 | 20 | μs |
| PEAK COIL ENERGY | $W_L = 1/2 L I_{pk}^2$ | 136 | 123 | 97 | 89 | 74 | 58 | 60 | 52 | J |
| ENERGY DISSIPATION/PULSE | $\Delta W_C$ | 160 | 142 | 21/48*** | 48 | 25 | 26 | 21 | 27 | J |
| W/IRON CORE | $\Delta W_C$ | 40 | 36 | 5/12*** | 12 | 6 | 7 | 5 | 7 | J |
| LOAD INTEGRAL | $\int I_L^3 dt$ | 2,483 | 2,217 | 503 | 1,693 | 859 | 797 | 517 | 352 | $A^3 s$ |
| W/IRON CORE | $\int I_L^2 dt$ | 621 | 554 | 126 | 423 | 215 | 199 | 129 | 88 | $A^2 s$ |
| MAX. MEMBRANE DEPOLARIZATION | $MAX(\Delta V_m)$ | 18 | 18 | 18 | 18 | 18 | 18 | 18 | 18 | mV |
| HYPERPOLARIZATION/DEPOLARIZATION RATIO | $-MIN(\Delta V_m)/MAX(\Delta V_m)$ | 0.25 | 0.22 | 0.37 | 0.81 | 0.83 | 0.27 | 0.50 | 0.65 | - |

(*) FOR BIPHASIC PULSES, RISE TIME EQUALS INTERVAL BETWEEN PEAK NEGATIVE AND PEAK POSITIVE CURRENT
(**) EFFECTIVE PW = TIME INTERVAL FROM ZERO TO PEAK NEURONAL MEMBRANE DEPOLARIZATION
(***) (ASSUMING IDEAL CONVERSION OF ENERGY FROM $C_2$ TO $C_1$ AFTER PULSE)/(ASSUMING 70% CONVERSION EFFICIENCY)

SYSTEMS AND METHODS FOR INDUCING ELECTRIC FIELD PULSES IN A BODY ORGAN

CROSS REFERENCE TO RELATED CASES

The present application is a national stage entry of International Application No. PCT/US2007/012825, filed May 31, 2007, which claims priority to, and the benefit of, U.S. patent application Ser. No. 11/729,517, filed Mar. 28, 2007, and also claims priority to, and the benefit of, U.S. Patent Application Ser. No. 60/814,277, filed Jun. 15, 2006, and U.S. Patent Application Ser. No. 60/905,561, filed Mar. 7, 2007, the entireties of both of which applications are hereby incorporated herein by reference.

FIELD

The disclosed subject matter relates to systems and methods for providing controllable pulse parameter magnetic stimulation that induces electric field pulses in a body organ.

BACKGROUND

Magnetic stimulation is a noninvasive tool for the study of the human brain and peripheral nerves that is being investigated as a potential therapeutic agent in psychiatry and neurology. When applied to the brain, this technique is commonly referred to as Transcranial Magnetic Stimulation (TMS). However, the term "TMS" is often used to refer to magnetic stimulation of other body organs as well. Therefore, the term TMS will be used hereinafter to refer to magnetic stimulation of the brain or other body organs.

In TMS, a pulsed current sent through a coil produces a magnetic field that induces an electric field in the brain, which can affect neuronal activity. A single TMS pulse can activate a targeted brain circuit. For example, a TMS pulse delivered to the motor cortex can result in a twitch of the associated muscles in the body. Further, a single TMS pulse can also disrupt neural activity. For example, a TMS pulse delivered to the occipital cortex can mask the perception of a visual stimulus. This allows researchers to probe brain circuits on a millisecond time scale.

A train of TMS pulses, referred to as repetitive TMS (rTMS), can produce excitatory or inhibitory effects which last beyond the stimulation interval. Repetitive TMS provides a means to study higher cognitive functions, and it could potentially be used as a therapeutic intervention in psychiatry and neurology.

The neural response to TMS is sensitive to the parameters of the stimulating TMS pulse. The pulse width (PW), shape (e.g., sinusoidal vs. rectangular), and the relative amplitude of the positive and negative phases (degree of bidirectionality) of the induced electric field affect the physiological response to TMS, the power efficiency of the stimulator, and the heating of the stimulating coil. Existing TMS systems are capable of inducing only damped cosine electric field pulse shapes, with a limited set of discrete choices of pulse width and degree of bidirectionality. Further, in existing TMS systems, monophasic magnetic field pulse shapes are associated with very low power efficiency of the stimulator in rTMS applications.

SUMMARY

Systems and methods are disclosed for providing controllable pulse parameter magnetic stimulation that induces electric field pulses in a body organ.

One aspect is directed to a magnetic stimulation system for inducing approximately rectangular electric field pulses in a body organ, comprising an electrical energy storage device, a stimulating coil, and a switching means for electrically coupling said electrical energy storage device to said stimulating coil to produce current pulses in said stimulating coil which generates, in response to the current pulses, magnetic field pulses that can induce approximately rectangular electric field pulses in the body organ.

Another aspect is directed to a magnetic stimulation system for inducing approximately rectangular electric field pulses in a body organ, comprising a first and a second electrical energy storage device, a stimulating coil, a first switching means to electrically couple said first electrical energy storage device to the stimulating coil to produce current pulses with a positive rate of change in the stimulating coil, and a second switching means to electrically couple said second electrical energy storage device to said stimulating coil to produce current pulses with a negative rate of change in the stimulating coil, wherein the stimulating coil produces, in response to a combination of the current pulses with the positive and negative rates of change, magnetic field pulses that can induce approximately rectangular electric field pulses in the body organ.

Another aspect is directed to a method of inducing approximately rectangular electric field pulses in a body organ with a magnetic stimulation system. The method comprises providing a first and a second energy storage device, providing a stimulating coil, providing a first switching means electrically coupled to the first energy storage device and the stimulating coil, providing a second switching means electrically coupled to the second energy storage device and the stimulating coil, actuating the first switching means to electrically couple the first energy storage device to the stimulating coil for a first period of time to produce current pulses with a positive rate of change in the stimulating coil, actuating the second switching means to electrically couple the second energy storage device to the stimulating coil for a second period of time to produce current pulses with a negative rate of change in the stimulating coil, and thereby causing the stimulating coil to produce, in response to a combination of the current pulses with the positive and negative rates of change, magnetic field pulses that can induce approximately rectangular electric field pulses in the body organ, and positioning the stimulating coil proximate to the body organ and exposing the body organ to the magnetic field pulses thereby inducing the approximately rectangular electric field pulses in the body organ.

Another aspect is directed to a magnetic stimulation system for inducing adjustable pulse width electric field pulses in a body organ, comprising an electrical energy storage device, a stimulating coil; and a switching means for electrically coupling said electrical energy storage device to said stimulating coil, to produce selectively-adjustable-width current pulses in said stimulating coil which generates, in response to the current pulses, magnetic field pulses that can induce selectively-adjustable-width electric field pulses in the body organ.

Another aspect is directed to a method of inducing adjustable pulse width electric field pulses in a body organ. The method comprises providing an electrical energy storage device, providing a switching means, providing a stimulating coil, and electrically coupling said electrical energy storage device to said stimulating coil with said switching means to produce selectively-adjustable-width current pulses in said stimulating coil which generates, in response to the current pulses, magnetic field pulses that can induce selectively-adjustable-width electric field pulses in the body organ.

Another aspect is directed to a magnetic stimulation system for inducing electric field pulses with an adjustable degree of bidirectionality in a body organ, comprising a first and a second electrical energy storage device, a charging means electrically coupled to the first and second electrical energy storage devices for charging the first electrical energy storage device to a selectable first voltage and charging the second electrical energy storage device to a selectable second voltage, a stimulating coil, a first switching means to electrically couple the first electrical energy storage device to the stimulating coil to produce current pulses with a positive rate of change in the stimulating coil, and a second switching means to electrically couple the second electrical energy storage device to said stimulating coil to produce current pulses with a negative rate of change in the stimulating coil, wherein the stimulating coil produces, in response to a combination of the current pulses with the positive and negative rates of change, magnetic field pulses that can induce electric field pulses in the body organ, the degree of bidirectionality being determined by the ratio of the selectable first voltage and the selectable second voltage.

Another aspect is directed to a method of inducing electric field pulses with an adjustable degree of bidirectionality in a body organ. The method comprises providing a first and a second electrical energy storage device, providing a charging means electrically coupled to the first and second electrical energy storage devices for charging the first electrical energy storage device to a selectable first voltage and charging the second electrical energy storage device to a selectable second voltage, providing a stimulating coil, providing a first switching means electrically coupled to the first electrical energy storage device and the stimulating coil, providing a second switching means electrically coupled to the second electrical energy storage device and the stimulating coil, setting a desired degree of bidirectionality by selecting respective amplitudes for the first and second voltages, the degree of bidirectionality being determined by the ratio of the selected first voltage and the selected second voltage, actuating said first switching means to electrically couple the first electrical energy storage device to the stimulating coil for a first period of time to produce current pulses with a positive rate of change in the stimulating coil, actuating said second switching means to electrically couple the second electrical energy storage device to the stimulating coil for a second period of time to produce current pulses with a negative rate of change in the stimulating coil, and thereby causing the stimulating coil to produce magnetic field pulses in response to a combination of the current pulses with the positive and negative rates of change; and positioning the stimulating coil proximate to the body organ and exposing the body organ to the magnetic field pulses thereby inducing electric field pulses in the body organ with the desired degree of bidirectionality.

Another aspect is directed to a magnetic stimulation system for inducing electric field pulses in a body organ, comprising an electrical energy storage device, a stimulating coil, a switching means for electrically coupling said electrical energy storage device to said stimulating coil to produce current pulses in said stimulating coil which generates, in response to the current pulses, magnetic field pulses that can induce electric field pulses in the body organ, the electric field pulses having a plurality of selectively adjustable parameters from a group consisting of amplitude, pulse width, degree of bidirectionality and pulse frequency; and an operator-controlled apparatus including means for independently controlling at least two of said parameters.

Another aspect is directed to a method for inducing electric field pulses in a body organ with a magnetic stimulation system. The method comprises providing an electrical energy storage device, providing a stimulating coil, electrically coupling said electrical energy storage device to said stimulating coil with a switching means to produce current pulses in said stimulating coil which generates, in response to the current pulses, magnetic field pulses that can induce electric field pulses in the body organ, the electric field pulses having a plurality of selectively adjustable parameters from a group consisting of amplitude, pulse width, degree of bidirectionality and pulse frequency, detecting physiological effects induced in the body organ by the electric field pulses, and controlling at least two of said parameters based on the detected physiological effects.

Another aspect is directed to a magnetic stimulation system for inducing approximately rectangular electric field pulses in a body organ, comprising an electrical energy storage device, a stimulating coil, and a switching circuit configured for electrically coupling said electrical energy storage device to said stimulating coil to produce current pulses in said stimulating coil which generates, in response to the current pulses, magnetic field pulses that can induce approximately rectangular electric field pulses in the body organ.

Another aspect is directed to a method for inducing approximately rectangular electric field pulses in a body organ, comprising storing electrical energy in an electrical energy storage device, generating with a stimulating coil magnetic field pulses that can induce electric field pulses in the body organ, and switchably electrically coupling the electrical energy storage device to the stimulating coil to produce current pulses in the stimulating coil which generates, in response to the current pulses, magnetic field pulses that can induce approximately rectangular electric field pulses in the body organ.

BRIEF DESCRIPTION OF THE DRAWINGS

FIG. 11 is a table of pulse performance metrics used to evaluate the efficiency of controllable pulse parameter transcranial magnetic stimulation pulses.

DETAILED DESCRIPTION

The disclosed subject matter provides, among other things, a controllable pulse parameter transcranial magnetic stimulation (cTMS) system that induces approximately rectangular electric field pulses in an organ of a body, such as a human brain for example. The amplitude, pulse width, and degree of bidirectionality of the induced electric field pulses are adjustable over a continuous range of values. The degree of bidirectionality is defined as the ratio of the positive phase amplitude to the negative phase amplitude of the induced electric field pulse. By adjusting the degree of bidirectionality, the induced electric field pulse can be varied from bipolar (i.e., equal amplitudes of the positive and negative phases) to predominantly unipolar (i.e., a large amplitude of one phase for one polarity and a small amplitude of the other phase for the opposite polarity).

In some embodiments, the cTMS system disclosed herein switches a stimulating coil between positive-voltage and negative-voltage energy storage capacitors or capacitor banks using high-power semiconductor devices. Controlling the pulse parameters facilitates enhancement of TMS as a probe of brain function and as a potential therapeutic intervention. Independent control over the pulse parameters (e.g., pulse width, pulse amplitude, degree of bidirectionality) facilitates defining dose-response relationships for neuronal populations and producing clinical and physiological effects. For example, dose-response relationships for specific neuronal populations can be defined, and selected clinical and physiological effects can be enhanced. Moreover, the cTMS system disclosed herein also enables high-frequency (≥1 Hz) repetitive TMS (rTMS) with predominantly unipolar induced electric fields.

Figure 1:
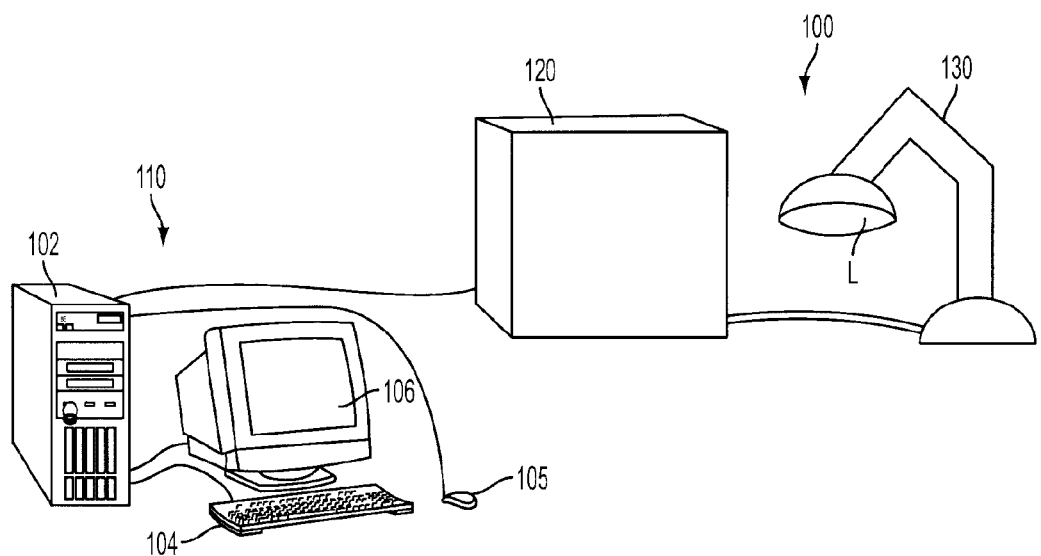
FIG. 1 is an illustrative component diagram of a controllable pulse parameter transcranial magnetic stimulation system, according to some embodiments of the disclosed subject matter.

Referring to FIG. 1, in one embodiment, an illustrative component diagram of a controllable pulse parameter transcranial magnetic stimulation system 100 is shown. The cTMS system 100 includes a power electronics housing 120, a positioning arm 130, a stimulating coil L, and a digital data processing device, such as control computer electronics 110. The control computer electronics 110 includes a control computer electronics housing 102 with a digital data processing device and a storage device (e.g., a hard disk), a keyboard 104, a monitor 106, and a mouse 105 (or trackball), and/or other data entry devices. The power electronics circuitry in housing 120 includes cTMS system power electronics that supply current to the stimulating coil L, which can be positioned and held proximate to a patient's head by the positioning arm 130. The power electronics circuitry in the power electronics housing 120 is controlled by the control computer electronics 110. An operator, operating the control computer electronics 110, controls the power electronics in power electronics housing 120 to produce one or more adjustable current pulses that are passed through the stimulating coil L held by positioning arm 130. During a medical treatment, the stimulating coil L is positioned proximate to a patient's head. The adjustable current pulses that are passed through the stimulating coil L result in the stimulating coil L generating adjustable magnetic field pulses, which induce adjustable electric field pulses which, in turn, induce adjustable current pulses in the patient's brain.

Figure 2A:
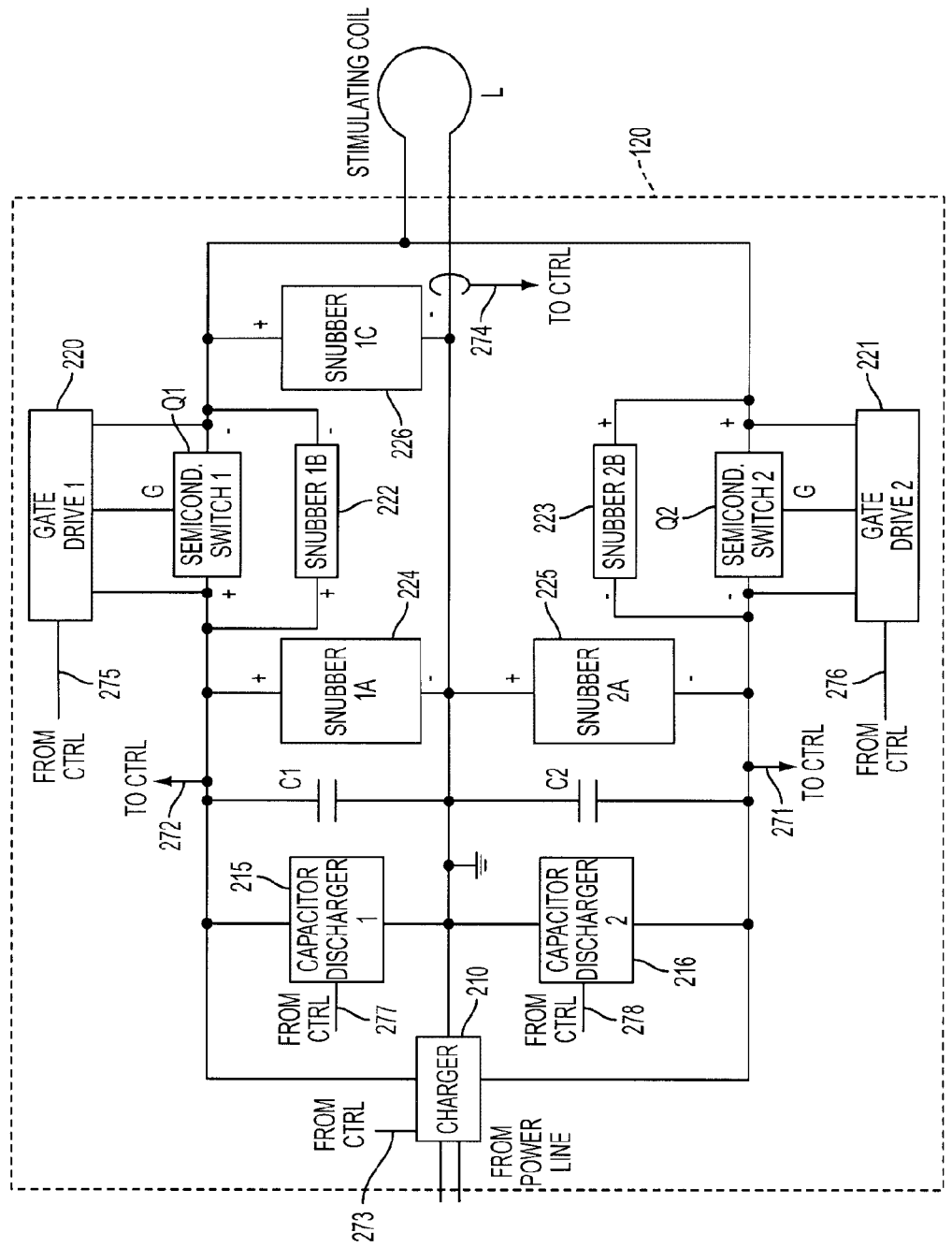
FIG. 2A is an illustrative block diagram of an embodiment of the power electronics circuitry for the controllable pulse parameter transcranial magnetic stimulation system of FIG. 1.
Figure 2B:
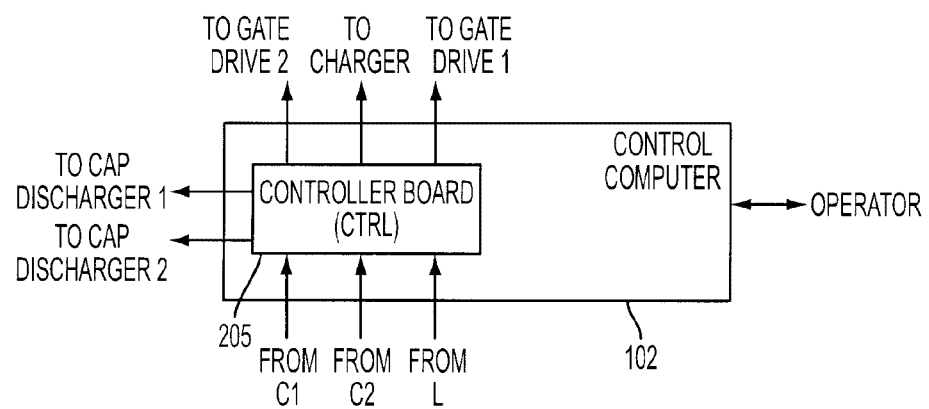
FIG. 2B is an illustrative block diagram of an embodiment of the control computer electronics for the controllable pulse parameter transcranial magnetic stimulation system of FIG. 1.

Referring to FIGS. 2A and 2B, illustrative block diagrams of embodiments of the power electronics circuitry in housing 120 and the control computer electronics in housing 102 are respectively shown. The power electronics housing 120 houses electronics used to drive the stimulating coil L. The electronics in the housing 120 include a charger 210, a first capacitor C1, a second capacitor C2, a first capacitor discharger 215, a second capacitor discharger 216, a first semiconductor switch Q1, a second semiconductor switch Q2, a first snubber circuit 222, a second snubber circuit 223, a third snubber circuit 224, a fourth snubber circuit 225, a fifth snubber circuit 226, a first gate drive 220, and a second gate drive 221.

The control computer housing 102 houses a typical central processing unit (CPU) (not shown), and various standard printed circuit board slots (not shown). Inserted into one of the slots is a controller board 205 that provides control signals used to control the cTMS system 100, and is discussed in further detail below.

In one embodiment, capacitor C1 and capacitor C2 are single capacitors. In another embodiment, capacitor C1 and capacitor C2 each represent a separate bank of capacitors. The capacitors in each separate bank are connected in parallel and/or in series with each other.

Figure 3A:
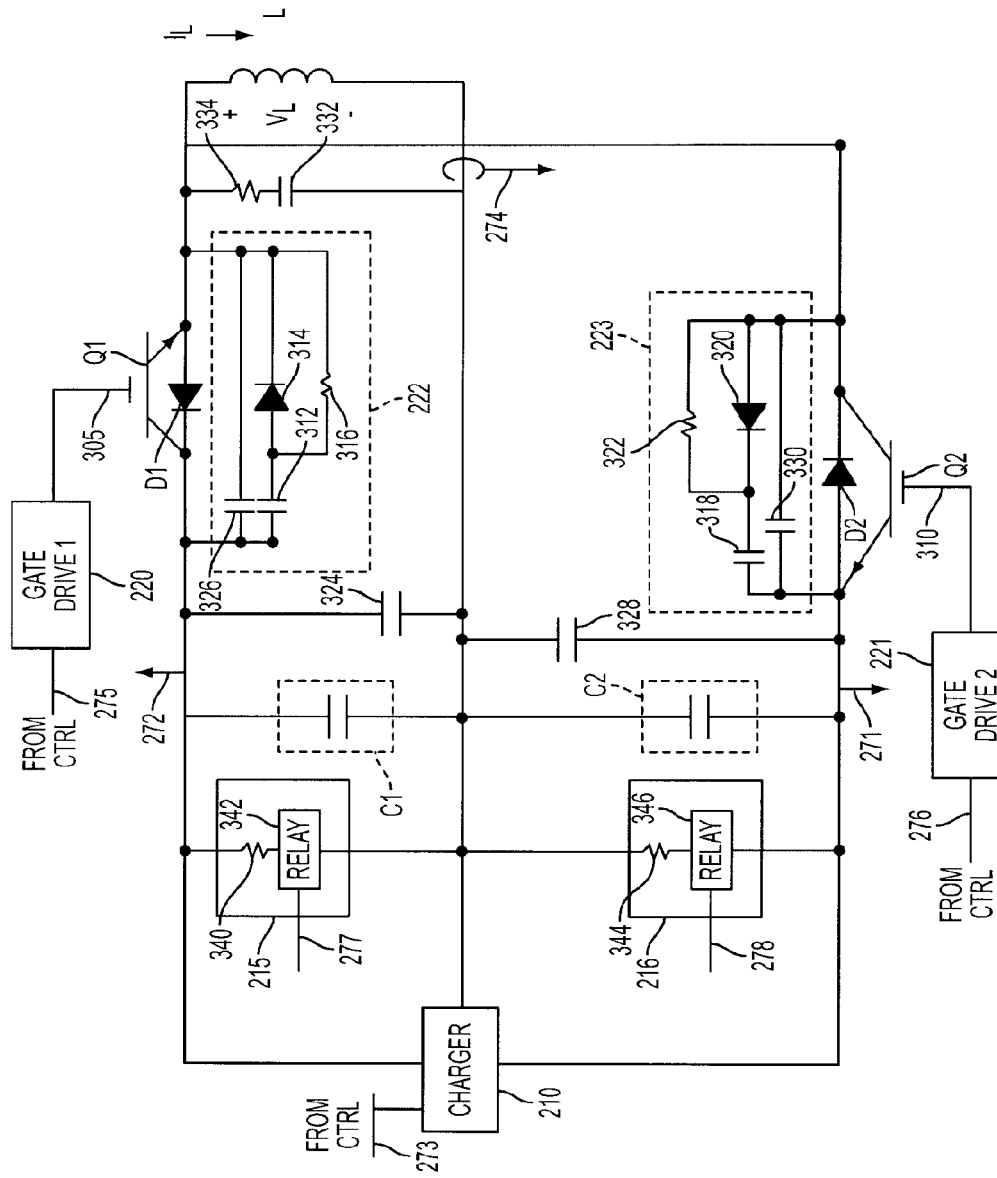
FIG. 3A is an illustrative schematic diagram of another embodiment of the power electronics circuitry for controllable pulse parameter transcranial magnetic stimulation circuit.

Referring to FIG. 3A, an illustrative schematic diagram of the controllable pulse parameter transcranial magnetic stimulation circuit for driving the stimulation coil L is shown. As previously described in connection with the block diagram of FIGS. 2A and 2B, the controllable pulse parameter transcranial magnetic stimulation circuit for driving the stimulation coil L includes energy storage capacitor (or bank of capacitors) C1, energy storage capacitor (or bank of capacitors) C2, controllable semiconductor switch Q1, controllable semiconductor switch Q2, the first and second gate drives 220, 221, and charger 210. The circuit of FIG. 3A additionally includes a diode D1 connected in anti-parallel with the controllable semiconductor switch Q1, and a diode D2 connected in anti-parallel with the controllable semiconductor switch Q2.

Referring again to FIGS. 2A, 2B, and 3A, in one embodiment, an operator controls the cTMS system using the control computer electronics 110. The operator selects cTMS system operation with monophasic or biphasic magnetic pulses and a desired set of induced electric field pulse parameters such as pulse amplitude (A), width of positive pulse phase (PW$^+$), width of initial negative pulse phase (PW$^-$ can be chosen for the biphasic pulse only), ratio of negative to positive capacitor voltage (M), which determines the degree of bidirectionality, and the frequency of pulse repetition ($f_{train}$) via a graphical user interface (discussed below) executing on the control computer 102. The selected values are stored in the control computer 102.

The controller board 205 is in communication with and controls the charger 210, the first gate drive 220, the second gate drive 221, and capacitor discharger 215 (which includes resistor 340 and normally closed relay 342) and capacitor discharger 216 (which includes resistor 344 and normally closed relay 346) via connections 273, 275, 276, 277, and 278, respectively. The controller board 205 is also in communication with, and receives data from, the energy storage capacitors C1 and C2, and the stimulating coil L via connections 272, 271, 274, respectively.

The charger 210 charges the energy storage capacitor C1 to a positive voltage $V_{C1}$ (set by the operator), and the energy storage capacitor C2 is charged to a negative voltage $-V_{C2}$ (set by the operator). The charger transfers energy from a power line to the capacitors, and transfers energy between the two capacitors. The positive and negative capacitor voltages are independently selectable. Voltage $V_{C1}$ is set based on the pulse amplitude (A) selected by the operator, and voltage $V_{C2}$ is set equal to $M*V_{C1}$, where M is the ratio of negative to positive capacitor voltage selected by the operator. The stimulating coil L is connected to capacitors C1 and C2 via the semiconductor switches Q1 and Q2, and diodes D1 and D2, respectively.

The controller board 205 also supplies separate sets of timing pulses with adjustable widths (set by the operator) to the first and second gate drives 220, 221. The first and second gate drives 220, 221 each use the timing pulses to produce separate sets of voltage pulses with adjustable widths.

In FIG. 3A, each semiconductor switch Q1 and Q2 includes a gate terminal 305 and 310, respectively. The gate terminals 305 and 310 are driven (i.e., clocked) by the voltage pulses supplied by the gate drives 220 and 221. The voltage pulses from controller board 205 are used to switch the semiconductor switches Q1 and Q2 to an on state or an off state. Anti-parallel connected diodes D1 and D2 transfer energy from the stimulating coil L back to capacitors C1 and C2, respectively.

The semiconductor switch Q1 connects coil L to energy storage capacitor C1 for an interval of time equal to the pulse width of the voltage pulses received at the gate terminal 305 from the first gate drive 220, which causes the coil current $I_L$ to increase during this interval of time. When semiconductor switch Q1 is turned off, the coil current commutates to capacitor C2 through diode D2, and the coil current starts to decrease until it reaches zero. Thus, turning switch Q1 on and off results in an approximately triangular positive coil current pulse, which induces an approximately triangular positive monophasic magnetic field pulse. This is discussed in further detail with respect to FIG. 4A. Likewise, the semiconductor switch Q2 connects coil L to energy storage capacitor C2 for an interval of time equal to the pulse width of the voltage pulses received at the gate terminal 310 from the second gate drive 221, which causes the coil current $I_L$ to decrease (i.e., become more negative) during this interval of time. When semiconductor switch Q2 is turned off, the coil current commutates to capacitor C1 through diode D1, and the coil current starts to increase (i.e., become more positive) until it reaches zero. Thus, turning switch Q2 on and off results in an approximately triangular negative coil current pulse, which produces an approximately triangular negative monophasic magnetic field pulse. This is discussed in further detail with respect to FIG. 4B. If an adjustable negative monophasic magnetic field pulse and an adjustable positive monophasic magnetic field pulse are both generated subsequently, an adjustable biphasic magnetic pulse is produced. The approximately triangular magnetic field pulses with adjustable widths induce approximately rectangular electric field pulses in an organ of a body. The approximately rectangular electric field pulses, in turn, induce approximately rectangular, adjustable-pulse-parameter current pulses in an organ of a body, such as a human brain, for example.

The controller board 205 provides timing signals with microsecond resolution to control the semiconductor switches. The cTMS system uses timing of the turn-on and turn-off transitions of the control signals for both semiconductor switches Q1 and Q2 to provide accurate pulse waveform control.

In one embodiment, the controller board 205 is a PCI card from National Instruments (Austin, Tex.) with additional interface electronics that provides sub-microsecond timing signals. Additional interface electronics includes signal conditioning and isolation circuits such as optocouplers, fiber optic links, isolation transformers, attenuators, amplifiers, and filters, as required to connect the controller board 205 to the power electronics in the power electronics housing 120. The PCI card (controller board 205) resides in the control computer housing 102 that provides a GUI for interfacing and configuring the controller board 205. The control computer housing 102 also houses a mass storage device, such as a hard disk (not shown) for storing data. The GUI is implemented in LabVIEW software (available from National Instruments Corp.). The operator inputs various pulse parameters, which are discussed in detail below. The controller board software computes the corresponding capacitor voltages ($V_{C1}$, $V_{C2}$) and switch timing. The controller board 205 then sends the capacitor voltage commands to the charger 210, capacitor dischargers 215, 216, and the switch timing signals to the gate drives 220, 221. The controller board 205 also samples $V_{C1}$, $V_{C2}$) and $I_L$, (via connections 271, 272, 274) to monitor circuit operation, and inhibits or prevents coil currents from exceeding specifications.

Typically, the controllable semiconductor switches Q1 and Q2 should be able to withstand the peak coil current and the peak voltages appearing across their terminals at the peak pulse repetition frequency. The switches Q1 and Q2 should also have turn-on and turn-off times of no more than a few microseconds. The maximum voltage of the semiconductor switches Q1 and Q2 is ideally $V_{C1}+V_{C2}$. However, during current commutation between the two energy storage capacitors C1 and C2, the switch voltage can overshoot this value due to stray inductance and the finite turn-off and turn-on times of the semiconductor switches Q1 and Q2, and diodes D1 and D2. To address this issue, semiconductor devices with fast switching times should be used.

Figure 3B:
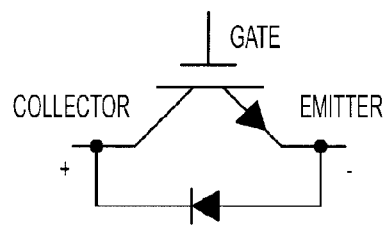
FIG. 3B is an illustrative schematic diagram of an insulated-gate bipolar transistor switch with an anti-parallel diode.
Figure 3C:
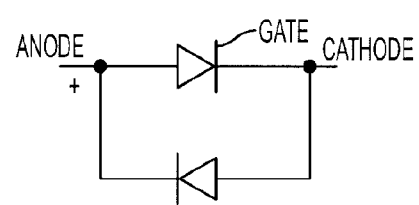
FIG. 3C is an illustrative schematic diagram of a gate turn-off thyristor with an anti-parallel diode.

In one embodiment, insulated gate bipolar transistors (IGBTs—shown in FIG. 3B and available from Powerex of Youngwood, Pa.) are used for the switches Q1 and Q2. In another embodiment, gate-turn-off thyristors (GTOs), such as integrated gate-commutated thyristors (IGCTs) (shown in FIG. 3C) are used for switches Q1 and Q2. Both of these devices can sustain pulse currents of thousands of amperes at voltages of a few kilovolts while turning on and off in a few microseconds. Since these devices can turn off while the coil current is not zero, they are used with the snubber circuits 222, 223, 224, 225, 226 (discussed in detail below) which absorb the energy of the commutation transients, thus inhibiting and/or preventing voltage overshoots that exceed the voltage ratings of the semiconductor switches, and energy dissipation in the semiconductor switches, which occurs during switching.

Unlike the silicon-controlled rectifiers (SCRs) used in conventional stimulators, IGBTs can be both turned on and off from the gate terminal. There are existing IGBT modules with peak voltage/surge current ratings of 3300 Volts/12000 Amperes, 4500 Volts/6000 Amperes, 4500 Volts/9000 Amperes, and 6500 Volts/6000 Amperes, and switching times of about one microsecond, which can be used to implement a cTMS system. These IGBT modules have an integrated ultrafast reverse diode between the emitter and the collector (e.g., D1 and D2 in FIG. 3), which clamps the IGBT reverse voltage, and provides a free-wheeling path for the coil current $I_L$.

IGCTs behave like efficient SCRs when turning on and during conduction, and behave like IGBTs when turning off. The turn-on time for an IGCT is approximately 1 µs, but the turn-off time can be as long as 10 µs. IGCTs with integrated reverse diodes (e.g., D1 and D2) and gate drives (e.g., gate drive 220, 221) are available with ratings of 4500 Volts and 17000 Amperes surge current, providing for robustness of the design.

In the cTMS system, the stimulating coil L is forced to commutate between the two energy storage capacitors C1 and C2 when the coil current is at its peak. Managing the forced commutation transient is a challenging aspect of implementing the cTMS system. The finite turn-off and turn-on times of the semiconductor switches Q1 and Q2, and the stray inductance in the capacitor banks C1 and C2, the switches Q1 and Q2, the diodes D1 and D2, and the wiring between them, can result in voltage overshoots that exceed the voltage ratings of the semiconductor switches, and switching power loss and heating in the semiconductor switches. The stray inductances are reduced and/or minimized by installing the semiconductor switches Q1 and Q2, the diodes D1 and D2, and the capacitor banks C1 and C2 as close together as allowed by the physical dimensions of the components, and interconnecting them with wires or bus bars arranged to minimize the area of the current loop. Still, stray inductance cannot be completely eliminated. For example, a typical capacitor bank series inductance of 150 nH with 7 kA current stores magnetic energy sufficient to produce a 27 kV spike on an IGBT switch with 10 nF collector capacitance, which would exceed the voltage rating of a 4500 V IGBT by 22500 V, resulting in potential damage to the IGBT. Therefore, the snubber circuits 222, 223, 224, 225, 226 are used to slow down the transients, ameliorate power dissipation in the semiconductor switches Q1 and Q2, and provide paths for stray inductances to discharge in order to suppress the voltage overshoots.

In one embodiment, as shown in FIG. 3A, the snubber circuits 222, 223 each include a capacitor 312, 318 in series with a diode 314, 320 and resistor 316, 322, which are in parallel with each other. Snubber circuits 222, 223 each also include capacitors 326, 330. This configuration allows the stimulating coil current to flow through the snubber capacitor 312, 318 when the corresponding semiconductor switch Q1, Q2 is turning off, thus inhibiting and/or preventing voltage overshoots. The snubber capacitor 312, 318 should be large enough to hold the peak switch voltage below its rated limit. If the snubber capacitor 312, 318 is too large, switching losses are increased. Snubber circuit 224 includes capacitor 324, snubber circuit 225 includes capacitor 328, and snubber circuit 226 includes capacitor 332 and resistor 334.

Figure 3D:
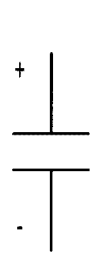
FIGS. 3D-3F are illustrative schematic diagrams of snubber circuits.
Figure 3E:
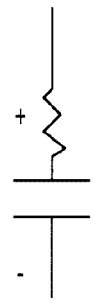
Figure 3F:
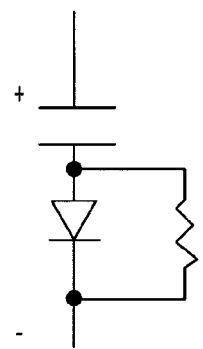

Snubber circuits 222 and 223 (see FIGS. 2A, 3A) can include the circuit embodiments shown in FIGS. 3D, 3E and/or 3F. Snubber circuits 224, 225, and 226 (see FIG. 2A) can include the circuit embodiments shown in FIGS. 3D and/or 3E.

Approaches for sizing of snubber components will be readily understood by those of ordinary skill in the art, and include, but are not limited to, approaches discussed in manufacturer application notes.

The gate drives 220, 221 serve to drive (clock) the semiconductor switches Q1 and Q2 to an on state or an off state. As previously discussed, the gate drives 220, 221 receive timing signals from the controller board 205, and apply gate voltages to the gates 305, 310. Some high-power switches, such a IGCTs, are manufactured with an integrated gate drive unit. IGBTs require a separate external gate drive. For high-power IGBTs, 10-20 µC is delivered to the gate to raise the gate-emitter voltage to 15-20 Volts to turn on the device. To switch the gate in about 1 µs, IGBT gate drives need an output impedance of a few ohms, and provide peak currents of a few Amperes. IGBT gate drives are available commercially. In some implementations, the gate drives 220, 221 incorporate short-circuit protection which prevents the switch from turning on if a short circuit is detected between the collector and emitter terminals (in IGBTs) or the anode and cathode terminals (in GTOs and IGCTs), which improves the fault tolerance and safety of the cTMS system.

The pulse width control parameters, PW⁺ and PW⁻ are limited by the discharge of C1 and C2, respectively. To enable pulse width control over a significant range (e.g., up to hundreds of microseconds) and to produce approximately rectangular induced electric field pulses, the energy storage capacitors C1 and C2, in most embodiments disclosed herein, have capacitances in the range of 300 to 800 µF, and 1000 to 3000 μF, respectively. These capacitance values can be accomplished with single pulse capacitors or with banks of parallel and/or series connected pulse capacitors. Suitable capacitor technologies for implementation of C1 and C2 use oil, polypropylene, and/or polyester dielectrics. For example, in one embodiment, C1 is implemented using two parallel 185 μF, 3 kV oil-filled pulse capacitors (e.g., General Atomics model 39504), and C2 is implemented using two parallel 750 μF, 1 kV oil-filled pulse capacitors (e.g., General Atomics model 310DM475). The maximum C1 voltage $V_{C1}$ is 2,800 V, and the minimum (maximum negative) C2 voltage—$V_{C2}$ is 900 V.

Whereas in conventional TMS systems the voltage on the energy storage capacitor is reversed during the pulse, in the disclosed cTMS system the voltages on the capacitors C1 and C2 are never reversed, i.e., always $V_{C1} \geq 0$ and $-V_{C2} \leq 0$. Capacitor voltage reversal decreases the capacitor life expectancy by as much as ten times. Therefore, the energy-storage capacitors C1 and C2 of the disclosed cTMS system have a longer life expectancy since no capacitor voltage reversal occurs.

The capacitor charger 210 for the cTMS system supplies energy to both the capacitors C1 and C2 at two independently controlled DC voltages, $V_{C1}$ and $V_{C2}$, respectively. The capacitor charger 210 also transfers energy from capacitor C2 to capacitor C1 to recover energy accumulated on capacitor C2 after a monophasic positive current pulse in coil L, corresponding to a positive monophasic magnetic field pulse. The capacitor charger 210 also transfers energy from capacitor C1 to capacitor C2 to recover energy accumulated on capacitor C1 after a monophasic negative current pulse in coil L, corresponding to a negative monophasic magnetic field pulse. In one embodiment, a charging unit such as the Magstim Super Charger (available from The Magstim Corp., Whitland, UK) is used to charge the positive capacitor C1. A bidirectional inverting DC/DC power supply is used to transfer energy between capacitor C1 and capacitor C2 so that $V_{C2}$ is maintained at a set level. Capacitor dischargers 215, 216, which constitute a resistor and a normally closed relay connected in series, are included and activated when the energy stored in capacitors C1 and C2 has to be reduced, such as when the pulse amplitude setting A is decreased by the operator, or when the energy stored in capacitors C1 and C2 has to be completely dissipated, such as when the cTMS system is shutdown, power is lost, or a system fault is detected by the controller.

A stimulating coil L known in the art is used with the cTMS system. Both air core and ferromagnetic core coils can be used with the cTMS system. A coil connector compatible with Magstim 200 coils is used to connect the stimulating coil L to the cTMS circuitry. In one embodiment, a Magstim 16.4 μH 70 mm double stimulating coil (commonly referred to in the art as a figure-of-8) is used.

Due to the rate of change and peak strength of the magnetic field required to achieve transcranial cortical stimulation, TMS systems operate at very high capacitor voltages (up to 3 kV) and peak coil currents (up to 10 kA). In one embodiment, the cTMS system employs maximum positive and negative capacitor voltages of 2800 Volts and −900 Volts, respectively, and a peak coil current of 7 kA.

The currents, voltages, and pulse widths applied to the energy storage capacitors C1 and C2, stimulating coil L, coil cable and connector, and internal wiring in the cTMS system typically do not exceed the currents, voltages, and pulse widths in conventional TMS systems. The cTMS system power consumption in rTMS operation typically does not exceed that of existing TMS systems, since commensurate pulse energies and pulse train frequencies are used. Further, given the higher electrical efficiency of triangular magnetic pulses, the peak values of the pulse parameters could be reduced in comparison with available stimulators. Thus, existing solutions for these system components can be used in the cTMS system.

Figure 4A:
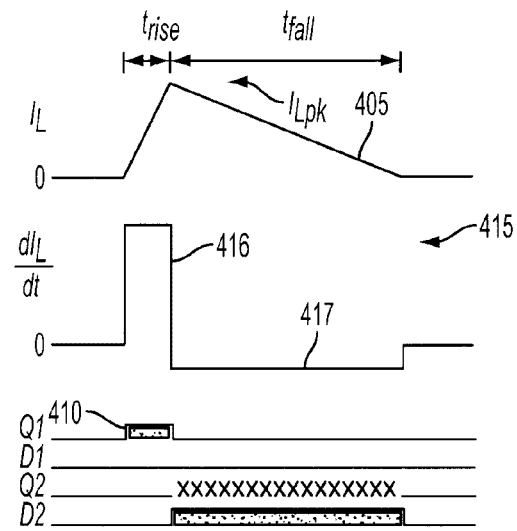
FIG. 4A is an illustrative graph of a positive magnetic pulse generated by using the controllable pulse parameter transcranial magnetic stimulation circuit of FIG. 3A.
Figure 4B:
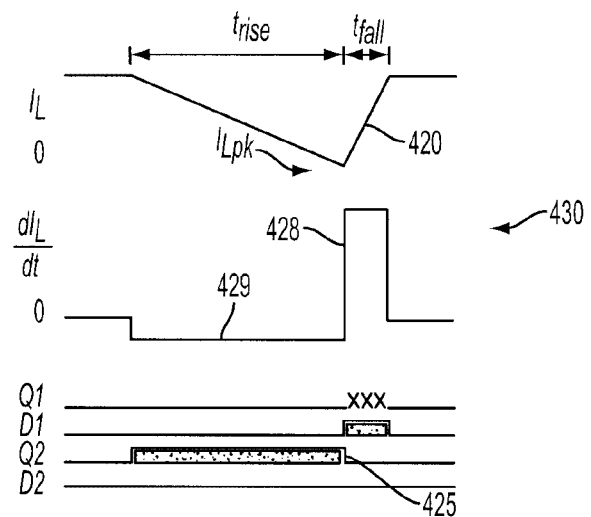
FIG. 4B is an illustrative graph of a negative magnetic pulse generated using the controllable pulse parameter transcranial magnetic stimulation circuit of FIG. 3A.

An analysis of the cTMS circuit shown in FIG. 3A will now be presented in connection with FIGS. 4A, 4B. For this analysis, it is assumed that storage capacitors C1 and C2 are large. Specifically, it is assumed that the following conditions are met:

$$t_{rise} << \pi/2 * (\text{inductance of coil } L * \text{capacitance of capacitor } C1)^{1/2} \text{ and}$$

$$t_{fall} << \pi/2 * (\text{inductance of coil } L * \text{capacitance of capacitor } C2)^{1/2},$$

where $t_{rise}$ and $t_{fall}$ are the rise and fall times of the magnetic field generated by the stimulating coil L. Further, in this analysis, the component parasitics and losses in the circuit are ignored. Under these conditions, the cTMS system induces approximately rectangular current pulses in the targeted body organ.

Referring to FIGS. 4A and 4B, in one embodiment, under the conditions specified above, graphs of positive and negative monophasic magnetic field pulses generated using the controllable pulse parameter transcranial magnetic stimulation circuit are shown. For this illustration, the ratio of the voltage across the capacitor C1 to the voltage across the capacitor C2 ($V_{C1}:V_{C2}$) is assumed to be 5:1. FIG. 4A depicts the generation of a positive magnetic field pulse 405, which is proportional to the current in the coil L.

When switch Q1 is switched to an on state 410, the resulting current ($I_L$) in the stimulating coil L increases at a rate of $dI_L/dt = V_{C1}/(\text{inductance of coil } L)$, as shown by waveform 416 in plot 415. Since capacitor C1 is very large, $V_{C1}$ stays approximately constant. After rise time $t_{rise}$, which is set by the operator by choosing when to turn Q1 on and off, switch Q1 is switched to an off state forcing the current $I_L$ in the stimulating coil L to commutate to capacitor C2 via the diode D2. While diode D2 is on, switch Q2 can be either on or off (referred to as a "don't care state" of the switch, and indicated with "x" symbols in the switch state waveforms). Since a negative voltage $-V_{C2}$ is now applied across the stimulating coil L, the stimulating coil current $I_L$ starts to decrease at a rate of $-V_{C2}/(\text{inductance of coil L})$ as shown by waveform 417 in plot 415. The coil current $I_L$ decays to zero in fall time $t_{fall}$, where trail: $t_{rise} = V_{C1}:V_{C2}$. Under ideal conditions, all the energy transferred from capacitor C1 to the stimulating coil L, which is equal to (inductance of coil L)$*I_{Lpk}^2/2$, is returned to capacitor C2, where $I_{Lpk}$ is the peak current in the coil L. Of course, as will be understood by those of ordinary skill in the art, losses will arise under ordinary (i.e., non-ideal) conditions, resulting in somewhat less than this amount of energy being transferred. This energy can be transferred back to capacitor C1 and reused in a subsequent pulse, which makes this strategy effective for repetitive TMS (rTMS).

FIG. 4B depicts the generation of a negative magnetic field pulse, which is proportional to the current in the coil L as previously described. When switch Q2 is switched to an on state 425, the resulting current ($I_L$) in the stimulating coil L decreases at a rate of $dI_L/dt = -V_{C2}/(\text{inductance of coil L})$, as shown by waveform 429 in plot 430. After rise time $t_{rise}$, which is chosen by the operator, switch Q2 is switched to an off state forcing the current $I_L$ in the stimulating coil L to commutate to capacitor C1 via the diode D1. While diode D1 is on, switch Q1 can be either on or off (referred to as a "don't care state" of the switch, and indicated with "x" symbols in the switch state waveforms). Since a positive voltage $V_{C1}$ is now applied across the stimulating coil L, the stimulating coil current $I_L$ starts to increase at a rate of $V_{C1}$/(inductance of coil L) as shown by waveform 428 in plot 430.

Figure 5A:
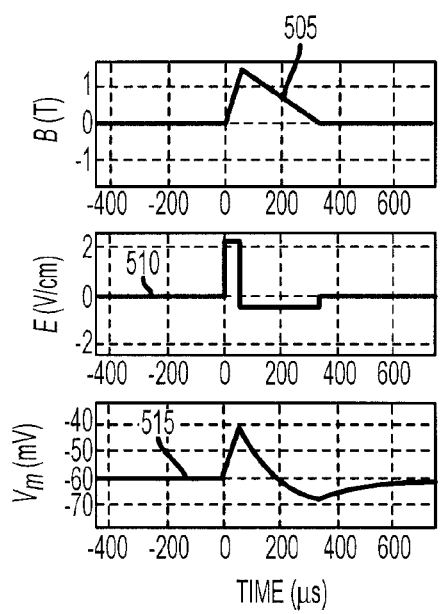
FIG. 5A shows illustrative waveforms of a monophasic magnetic field pulse (B), an associated electric field (E), and neuronal membrane voltage ($V_m$) induced in the brain by a controllable pulse parameter transcranial magnetic stimulation system, according to one embodiment of the disclosed subject matter.
Figure 5B:
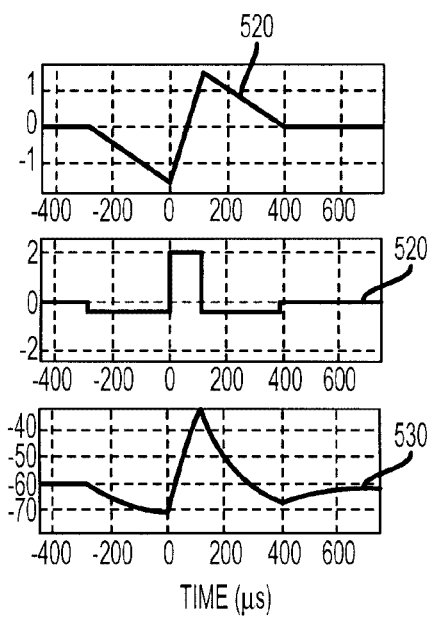
FIG. 5B shows illustrative waveforms of a biphasic magnetic field (B), an associated electric field (E), and neuronal membrane voltage ($V_m$) induced in the brain by a controllable pulse parameter transcranial magnetic stimulation system, according to one embodiment of the disclosed subject matter.

When the cTMS system is operated in monophasic magnetic pulse mode, as shown in FIG. 5A, the energy exchange between the storage capacitors C1 and C2 is implemented using charger circuit 210 to transfer energy from capacitor C2 to C1, or from capacitor C1 to C2 between pulses. When the cTMS system is operated in biphasic magnetic pulse mode, as shown in FIG. 5B, the energy exchange between the storage capacitors C1 and C2 is implemented by having a negative magnetic pulse precede a positive magnetic pulse. The energy from the storage capacitor C1 at the beginning of the pulse is returned to the storage capacitor C1 by the end of the pulse. The capability to operate in both monophasic and biphasic magnetic pulse modes enables optimization of the pulse type for specific research and clinical applications of the cTMS system.

Referring to FIG. 5A, in one embodiment, illustrative monophasic waveforms of a magnetic field pulse (B) 505, an electric field (E) 510, and a neuronal membrane voltage ($V_m$) 515, induced in the brain by the controllable pulse parameter transcranial magnetic stimulation system are shown.

As previously described, during a medical treatment, the stimulating coil L is positioned proximate to a patient's head. Adjustable current pulses are passed through the stimulating coil L and cause the stimulating coil L to generate adjustable magnetic field pulses. The adjustable magnetic field pulses induce adjustable electric field pulses which, in turn, induce adjustable current pulses in the patient's brain. The induced adjustable current pulses in the patient's brain result in voltage change on the neuronal membrane that can be measured.

The waveforms shown in FIG. 5A are produced by the current $I_L$ (plot 405) in the stimulating coil L shown in FIG. 4A. As previously described, the magnetic field B (plot 505) is proportional to the current $I_L$ in the stimulating coil L, and thus also has a triangular shape. The induced electric field E (plot 510) is proportional to the magnetic field rate of change (dB/dt), and correspondingly has a rectangular shape, rather than the cosine shape of existing TMS systems. Different rising and falling slopes of the magnetic field B (plot 505) result in different magnitudes of the positive and negative phases of the induced electric field E (plot 510), respectively. As previously described, the rate of change of the coil current ($dI_L/dt$) and, therefore, the rate of change of the magnetic field (dB/dt) is proportional to the voltage across the coil L. The voltage across the coil L is equal to the voltage of the capacitor to which the coil is connected. Therefore, the ratio of peak positive to negative electric field E is $V_{C1}$:$V_{C2}$. This is true in general, even when the circuit non-idealities are considered. Since the induced electric field pulse has a rectangular shape, and due to the neuronal membrane capacitance, the neuronal membrane voltage ($V_m$) follows a decaying exponential curve characterized by the membrane time constant, as shown by plot 515. If the neuronal membrane is depolarized (i.e., made more positive) by more than approximately 15 mV relative to its resting potential (−60 to −70 mV), the neuron is likely to produce an action potential (i.e., to fire).

Referring to FIG. 5B, in one embodiment, illustrative waveforms of a biphasic magnetic field (B) 520, and the associated electric field (E) 525 and neuronal membrane voltage ($V_m$) 530 induced in the brain by the controllable pulse parameter transcranial magnetic stimulation system are shown. Although the magnetic field B of plot 520 is biphasic with symmetric positive and negative phases, the induced electric field (plot 525) has a large positive amplitude and a comparatively small negative amplitude, since the rate of change of the rising magnetic field is much larger than the rate of change of the falling magnetic field. As a result (plot 530), the depolarization amplitude (as the neuronal membrane is made more positive) is larger than the hyperpolarization amplitude (as the neuronal membrane is made more negative). This example demonstrates how the cTMS system can produce predominantly unipolar electric field pulses and neuronal membrane voltage changes with biphasic magnetic pulses. In contrast, conventional sinusoidal biphasic magnetic pulses induce electric fields and neuronal membrane voltage changes that are bipolar (i.e., have approximately equal amplitudes of the positive and negative phases of the electric pulse). Biphasic magnetic pulses are more electrically efficient and produce less coil heating than monophasic magnetic pulses. Further, TMS biphasic magnetic pulses can be used inside a magnetic resonance imaging (MRI) scanner, since the torque on the wire loops of the stimulating coil L in the strong magnetic field of the scanner averages to approximately zero. In contrast, monophasic pulses cannot be used in an MRI scanner, since the average toque on the coil loops is non-zero, resulting in high mechanical stress in the coil that can damage the coil.

Figure 6:
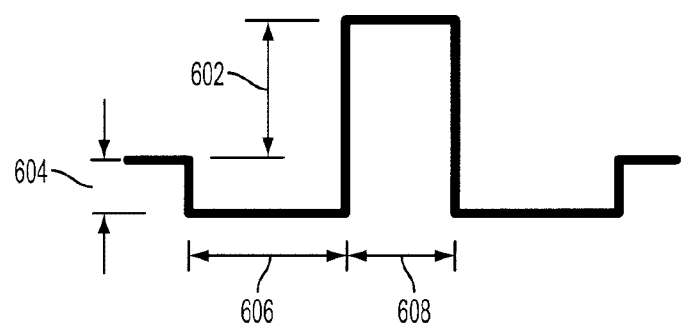
FIG. 6 is an illustrative waveform depicting user-adjustable pulse parameters, according to one embodiment of the disclosed subject matter.

Referring to FIG. 6, in one embodiment, an illustrative waveform depicting user-adjustable pulse parameters is shown. The user-adjustable parameters include: induced positive electric field amplitude (A) 602 (which corresponds to the intensity setting on conventional TMS systems), the pulse width of the positive phase ($PW^+$) 608, the induced negative electric field amplitude ($M^*A=(V_{C2}/V_{C1})^*A$) 604, which is specified through M, the ratio of negative to positive capacitor voltage, and the frequency of the pulse repetition ($f_{train}$). For biphasic operation, the duration of an initial negative electric field phase ($PW^-$) 606 can also be specified ($PW^-=PW^+/2M$ for symmetric negative side lobes of the pulse).

Figure 7:
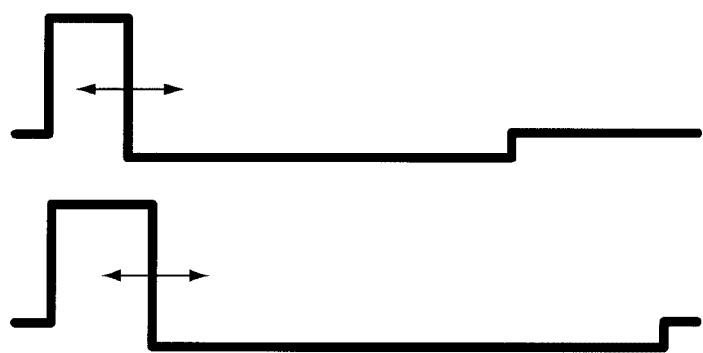
FIG. 7 shows illustrative waveforms of approximately rectangular induced electric field pulses with pulse widths adjustable over a continuous range of values, generated by a controllable pulse parameter transcranial magnetic stimulation circuit, according to one embodiment of the disclosed subject matter.

Referring to FIG. 7, in one embodiment, illustrative waveforms of approximately rectangular, predominantly unipolar current pulses with adjustable pulse width are shown. Control over the pulse width ($PW^+$) of the induced electric field pulse is accomplished by controlling the on and off timing of the semiconductor switches Q1 and Q2.

Figure 8:
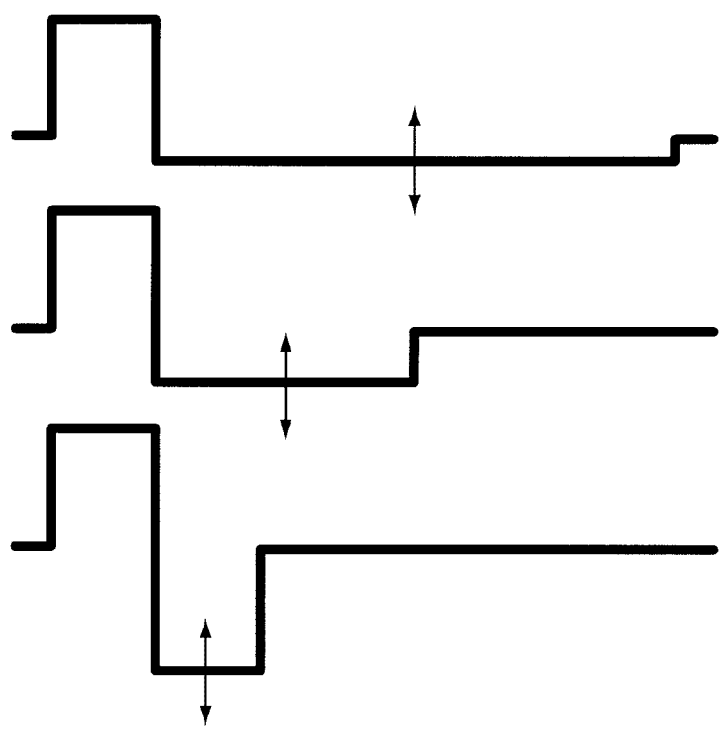
FIG. 8 shows illustrative waveforms of approximately rectangular induced electric field pulses with bidirectionality adjustable over a continuous range, generated by a controllable pulse parameter transcranial magnetic stimulation circuit, according to one embodiment of the disclosed subject matter.

Referring to FIG. 8, in one embodiment, illustrative waveforms depicting user-adjustable degree of bidirectionality of approximately rectangular electric field pulses are shown. Control over the degree of bidirectionality is accomplished by adjustment of the voltages of energy storage capacitors C1 and C2 relative to each other.

Figure 9:
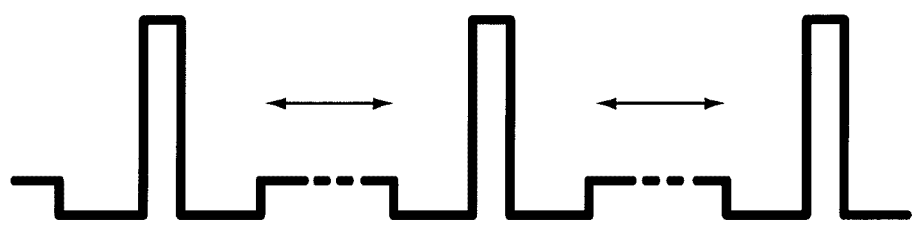
FIG. 9 is an illustrative waveform of repetitive TMS with predominantly unipolar induced electric field pulses, with adjustable pulse repetition frequency, according to one embodiment of the disclosed subject matter.

FIG. 9 shows an illustrative waveform of rTMS with a predominantly unipolar induced electric field. Computer simulations of a representative implementation of the cTMS system (FIG. 10) indicate that the cTMS pulses can induce membrane depolarization and hyperpolarization equal to that of commercial monophasic stimulators at only 16-18% of the power dissipation. This results in a reduction of power supply demands, heating, noise, and component size, and enables the cTMS system to produce high-frequency rTMS with predominately unipolar induced electric fields.

Figure 10:
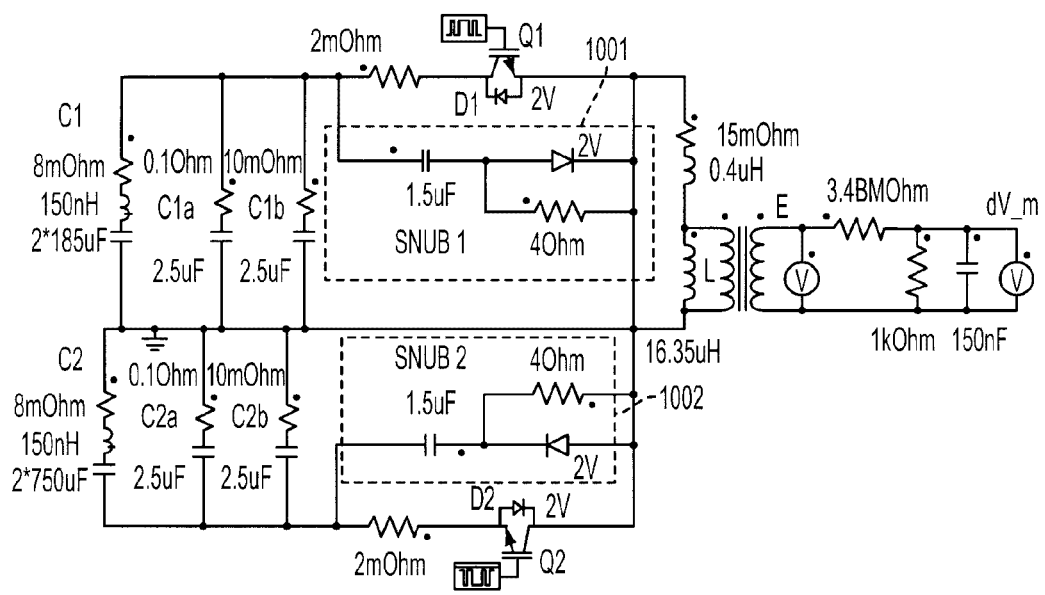
FIG. 10 is an illustrative simulation circuit for producing controllable pulse parameter transcranial magnetic stimulation, in accordance with the disclosed subject matter.

The cTMS system described in the disclosed subject matter was simulated and compared to existing TMS systems. A schematic of the cTMS simulation circuit is shown in FIG. 10. Further, a set of pulse performance metrics, i.e. performance figures, used to evaluate the efficiency of cTMS pulses compared to conventional pulse configurations of commercial TMS systems is shown in FIG. 11. The values were derived from computer simulations using PSIM circuit simulation software (available from Powersim Inc.) and the simulation circuit shown in FIG. 10.

Realistic component values are used. As previously described, snubber circuits 1001 and 1002 are added across the semiconductor devices Q1 and Q2, snubber capacitors C1a and C1b are added across the capacitor bank C1, and snubber capacitors C2a and C2b are added across capacitor bank C2 to handle transient energy.

Figure 12A:
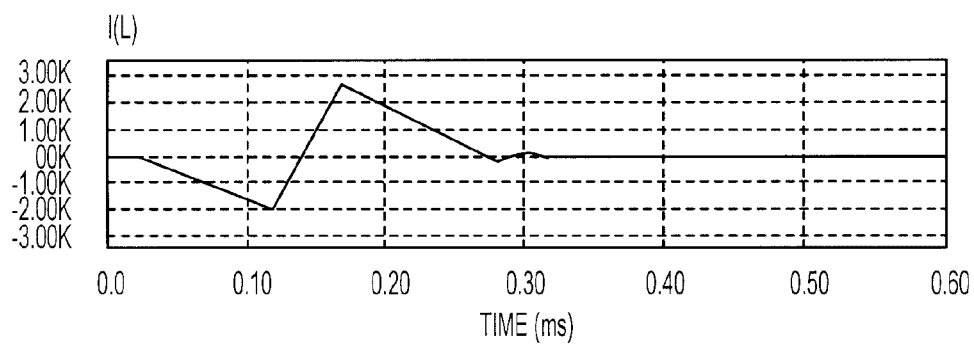
FIG. 12A shows an illustrative waveform of a stimulated coil current produced by the simulation circuit of FIG. 10.
Figure 12B:
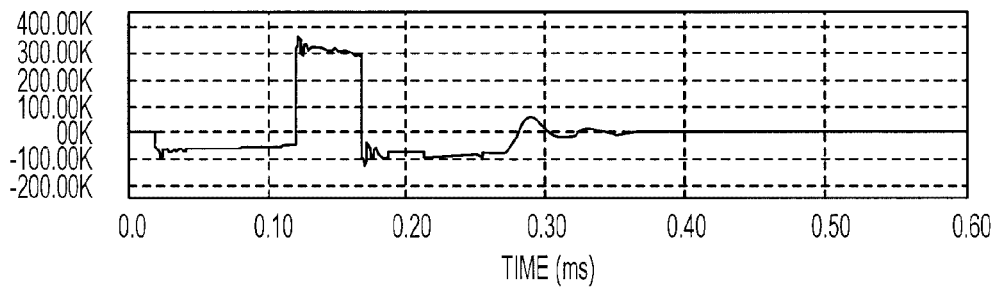
FIG. 12B shows an illustrative waveform of a stimulated peak induced electric field produced by the simulation circuit of FIG. 10.
Figure 12C:
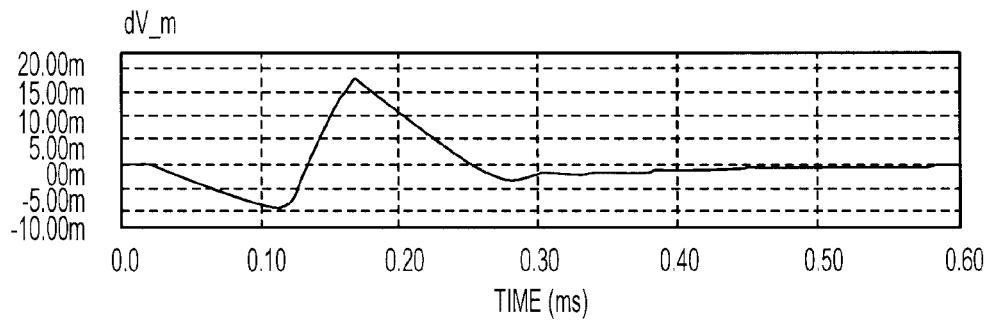
FIG. 12C shows an illustrative waveform of a stimulated estimated neuronal membrane voltage change produced by the simulation circuit of FIG. 10.

Waveforms showing the coil current I(L), peak induced electric field (E), and estimated neuronal membrane voltage change (dV_m) corresponding to the cTMS configuration shown in FIG. 10 are shown in FIGS. 12A, 12B, and 12C, respectively.

To allow a valid comparison of the pulse shape efficiency, all configurations use a model of Magstim "figure-of-8", air-core coil (L=16.4 µH), parasitic series resistance and inductance of 25 mΩ and 0.6 µH, and neuronal membrane time constant $\tau_m$=150 µs. The actual Neuronetics 2100 and Medtronic MagPro X100 systems use different coils than the Magstim figure-of-8 used in the comparison. Therefore, for the calculations for these systems, the capacitance was adjusted to match their typical pulse periods of approximately 200 and 270 µs, respectively, for the given 16.4 pH coil, because the objective is to compare the waveform efficiency rather than the actual commercial systems and coils.

To account for the higher efficiency of ferromagnetic (iron) core coils, standard with the Neuronetics 2100 machine, the total energy loss per pulse and the load integral (proportional to coil heating) are recalculated for an iron core coil, as indicated in FIG. 11. The iron core proportionally increases the efficiency of all pulse configurations, and can be used with the cTMS system to improve efficiency. Four representative cTMS pulse configurations are simulated (see columns cTMS$^1$-cTMS$^4$ of FIG. 11). For biphasic cTMS pulses (cTMS$^2$-cTMS$^4$), the duration of the initial negative phase was set to PW$^-$=PW$^+$/2M. The amplitude of the commercial device (Magstim, MagPro, Neuronetics) pulses is adjusted to produce equal neuronal membrane depolarization of $\Delta V_m$=18 mV, which is 20% above the assumed neuronal firing threshold of 15 mV depolarization. The amplitude and pulse width of the cTMS pulse configuration are also adjusted to produce identical neuronal membrane depolarization of $\Delta V_m$=18 mV.

FIG. 11 shows that the cTMS system can produce predominantly unipolar neuronal membrane potential change with both monophasic (cTMS$^1$) and biphasic (cTMS$^2$-cTMS$^4$) magnetic field pulses. For example, the cTMS$^2$ pulse configuration yields a membrane hyperpolarization/depolarization ratio of 0.27, which is comparable to that of the Magstim 200 and MagPro X100 (monophasic mode), while dissipating only 16% and 18% of the energy, respectively. The energy dissipation per pulse was calculated using the following equation:

$$\Delta W_C = \left(1/2 \sum_{\substack{\text{sum of all} \\ \text{capacitors} \\ \text{before pulse}}} Ci(V_{Ci})^2\right) - \left(1/2 \sum_{\substack{\text{sum of all} \\ \text{capacitors} \\ \text{after pulse}}} Ci(V_{Ci})^2\right),$$

where Ci refers to all capacitors in the stimulator power electronics, and where capacitor Ci has voltage $V_{Ci}$.

Further, coil heating (proportional to the load integral $I_L^2$dt) with the cTMS$^2$ pulse is only 32% and 36% that of the Magstim 200 and MagPro X100, respectively cTMS is able to achieve a total energy dissipation $\Delta W_C$ comparable to efficient biphasic systems, such as the Neuronetics 2100, with 8-59% less coil heating (load integral) while adding the previously unavailable functionalities of control over the induced electric field pulse width, degree of bidirectionality, approximately rectangular shape, and predominantly unipolar electric field pulses. It should be noted that for very brief, high-intensity rectangular pulses (cTMS$^4$), the coil heating decreases dramatically, while the total energy dissipation increases slightly. This is due to energy loss in the cTMS snubber circuits, which is proportional to the square of the capacitor voltage. However, since it is easier to cool the snubber circuits, which are inside the power electronics enclosure, than the coil, the reduced coil heating of brief, rectangular, high-voltage pulses can be advantageous in high-power applications such as magnetic seizure therapy (MST) where coil heating is currently the bottleneck for pulse train duration. Finally, in this model we have not accounted for ferromagnetic core losses, which could be higher for briefer pulses.

When monophasic magnetic field pulses are generated, energy is transferred from capacitor C1 to C2, and has to be transferred back to C1 by the power supply before the subsequent pulse in repetitive TMS (rTMS) operation. However, if a biphasic magnetic pulse is used to produce a predominantly unipolar electric field pulse, as shown in FIG. 5 and FIG. 12A-C, energy is transferred from C2 to C1 and then back from C1 to C2 during the pulse. Thus, there is no need for rebalancing a large amount of energy between the capacitors before the subsequent pulse, except for "topping off" the capacitors to compensate for the energy dissipated in losses during the pulse, as is the case in conventional biphasic TMS systems. With both monophasic and biphasic cTMS magnetic field pulses, the energy returning from the coil after each pulse is recycled, unlike that in conventional monophasic converters, which is dissipated in a resistor. However, compared to cTMS biphasic magnetic field pulses, monophasic magnetic field pulses require higher power capability of the cTMS power supply circuit that moves charge between the two capacitors.

Thus, the cTMS system is particularly well suited to generate high-frequency trains of predominantly unipolar electric field pulses. Using the results in FIG. 11, the unipolar rTMS power dissipation and coil heating of cTMS can be compared to that of conventional monophasic stimulators. The cTMS$^2$ configuration is 5-6 times more efficient and has about three times less coil heating than the Magstim 200 and MagPro X100 while producing the same neuronal depolarization and comparable hyperpolarization/depolarization ratio. For a pulse train frequency of 10 Hz, the Magstim 200, MagPro X100, and cTMS$^2$ pulse configurations described in FIG. 11 dissipate 1600, 1420, and 260 W, respectively, while the coil dissipation, assuming coil resistance of 10 mΩ, is 248, 222, and 80 W, respectively. If an iron-core coil is used, cTMS energy dissipation and coil heating can be further reduced to about 65 and 20 W, respectively. Therefore, with its substantially lower power dissipation and coil heating, the cTMS system can enable rTMS with predominantly unipolar electric field pulses. Recent research has indicated that rTMS with predominantly unipolar electric field pulses may have a stronger modulating effect on brain function, and, therefore, could be a more effective therapeutic intervention.

Figure 13A:
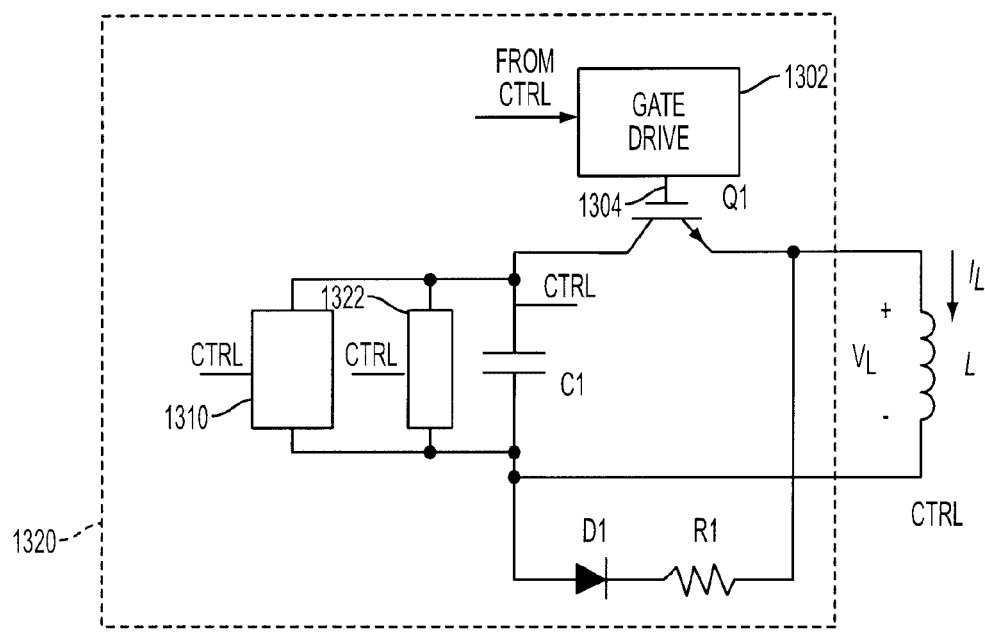
FIG. 13A is an illustrative block diagram of power electronics circuitry for a controllable pulse parameter transcranial magnetic stimulation system, according to another embodiment of the disclosed subject matter.
Figure 13B:
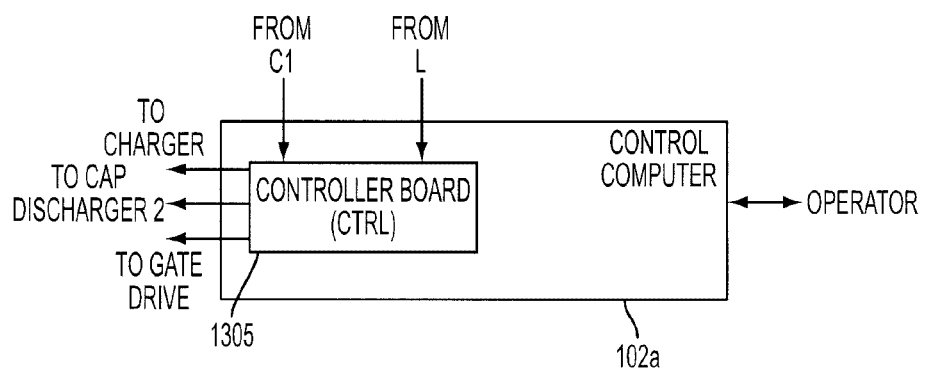
FIG. 13B is an illustrative block diagram of another embodiment of the control computer electronics for the controllable pulse parameter transcranial magnetic stimulation system.

Referring to FIGS. 13A and 13B, in an alternative embodiment, illustrative block diagrams of power electronics and a control computer system 102a for a controllable pulse parameter transcranial magnetic stimulation (cTMS) system are shown. The cTMS system includes a cTMS circuit 1320 for driving a stimulating coil L. The cTMS circuit 1320 includes energy storage capacitor (or bank of capacitors) C1, controllable semiconductor switch Q1, a gate drive 1302, charger 1310, capacitor discharger 1322, diode D1, and resistor R1. The cTMS system further includes a digital data processing device, such as control computer system 102a, which includes a controller board 1305.

This particular embodiment enables adjustment of the amplitude and the pulse width of the induced electric field over a continuous range of values, and the induced electric field pulses have an approximately rectangular shape. The semiconductor switch Q1 is implemented with an IGBT, which unlike an SCR, can be turned off from a gate terminal 1304. Further, the diode D1 and the energy dissipation resistor R1 are connected across the TMS coil L, to provide a discharge path for the coil current when Q1 is turned off. The energy storage capacitor C1 is larger than those used in conventional TMS stimulators to provide a wider range of pulse width control and approximately rectangular induced electric field pulses.

Similar to the cTMS circuit described in connection with FIGS. 2A, 2B, and 3A, the cTMS circuit 1320 shown in FIG. 13A is controlled by the controller board 1305 shown in FIG. 13B, which resides in the control computer 102a. Through the controller board 1305, the operator specifies the voltage of capacitor C1, which determines the amplitude of the induced electric field. The operator also specifies the on time and the off time of switch Q1, which determine the pulse timing and the pulse width (PW$^+$).

Figure 14:
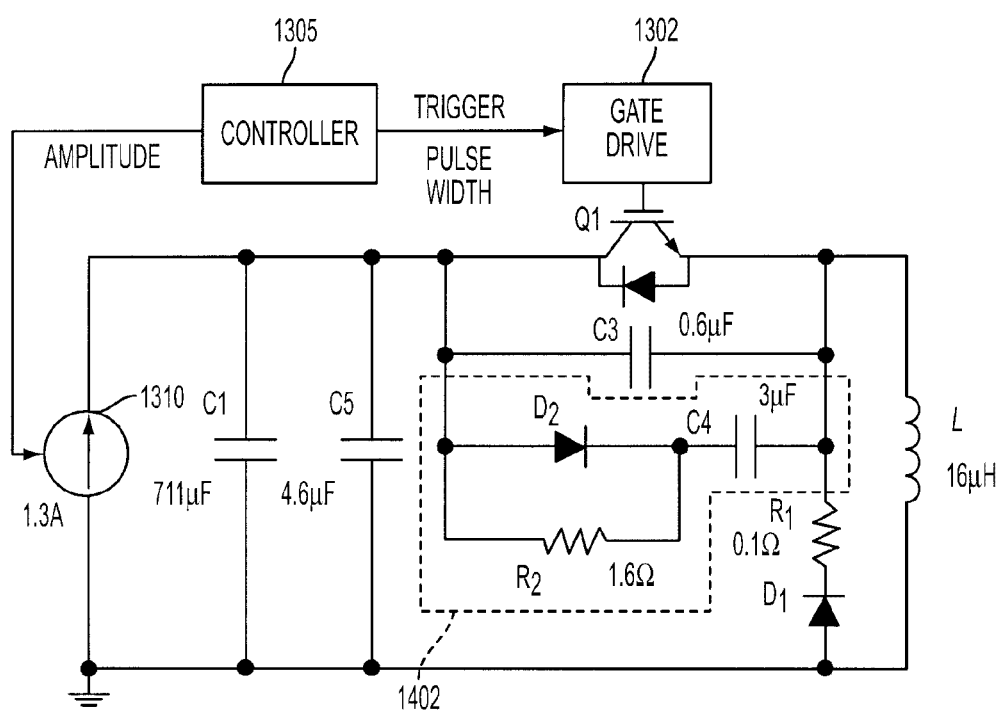
FIG. 14 is an illustrative schematic of a controllable pulse parameter transcranial magnetic stimulation circuit, according to another embodiment of the invention.

Referring to FIG. 14, in another embodiment, a schematic diagram of the cTMS circuit is shown. Stray inductance in the critical high-current paths of the circuit can cause power loss and voltage spikes during turn-off of switch Q1, which can cause component damage, as previously discussed. Therefore, the wiring and component locations in the cTMS circuit are arranged to reduce and/or minimize the stray inductance. However, stray inductances cannot be completely eliminated. Therefore, the cTMS circuit includes a number of snubber components. The snubber components assist the coil current commutation between the switch Q1 and the diode D1 and inhibits and/or prevents voltage overshoots and energy dissipation in the semiconductor switch Q1. A snubber capacitor or combination of capacitors C5 is mounted between the collector terminal of switch Q1 and the anode terminal of diode D1 to prevent the collector voltage from spiking during switch Q1 turn-off as a result of parasitic inductance of the capacitor bank C1 and the connecting wires. A capacitor C3 is mounted between the collector and emitter terminals of the switch Q1 to suppress high-voltage spikes across the terminals of switch Q1. A snubber circuit 1402, which includes diode D2, capacitor C4, and resistor R2, transiently absorbs the current flowing through the coil L when Q1 is turned off. This supports the current commutation to diode D1 and resistor R1, as previously discussed.

The energy storage bank of capacitors C1 comprises six 118 μF. (average measured value) oil-filled pulse capacitors. The bank of capacitors C1 is charged by a Magstim Booster Module Plus (The Magstim Co., Whitland, UK) and a Magstim capacitor voltage control circuit. The semiconductor switch Q1 is a 4500 Volt/600 Amp (direct current rating) IGBT module from Powerex, Inc. (Youngwood, Pa.). The IGBT (switch Q1) is controlled with a high-voltage optically-isolated gate drive 1302 by Applied Power Systems, Inc. (Hicksville, N.Y.). The controller board 1305 sends triggering pulses to the gate drive 1302. As previously described, the pulse width is set by the operator. The diode D1 is implemented with two series-connected, fast 1800 Volt/102 Amp (direct current rating) diodes by Semikron GmbH (Nuremberg, Germany). The snubber capacitors C3-C5 are high-voltage, high-current polypropylene film and paper film/foil capacitors. The snubber diode D2 includes three series-connected fast-recovery 1200 Volt/60 Amp (direct current rating) diodes from International Rectifier (El Segundo, Calif.). The stimulating coil L is a custom-made Magstim 5.5 cm mean diameter round coil with an inductance of 16 μH.

The cTMS circuit of FIG. 14 was tested with capacitor voltages of up to 1650 Volts, and peak coil currents of up to 7 kA. The peak intensity (i.e. amplitude of the electric field) of the cTMS system is equal to that of commercial Magstim Rapid stimulators. Unlike conventional stimulators, however, the cTMS system of the disclosed subject matter allows pulse width control with a range between 5 μs and 160 μs.

The electric field induced by the cTMS system was estimated with a single-turn 5 cm diameter search coil placed two centimeters from the face of the cTMS coil L. The search coil was connected to a digitizing oscilloscope as well as to a first-order low-pass filter with 150 μs time constant, which outputs a scaled estimate of the neuronal membrane voltage waveform.

Figure 15A:
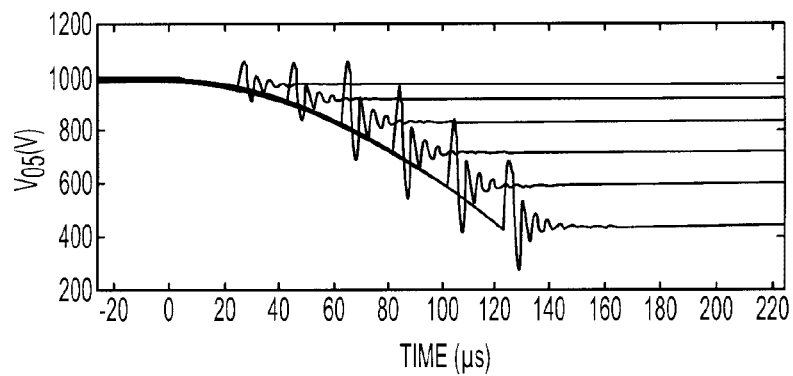
FIG. 15A shows illustrative waveforms of voltage across capacitor $C_5$ for different pulse widths of the controllable pulse parameter transcranial magnetic stimulation circuit of FIG. 14.
Figure 15B:
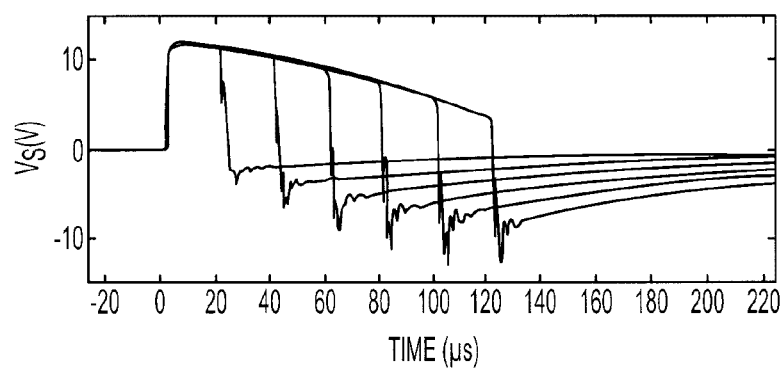
FIG. 15B shows illustrative waveforms of voltage induced in the coil L for different pulse widths of the controllable pulse parameter transcranial magnetic stimulation circuit of FIG. 14.
Figure 15C:
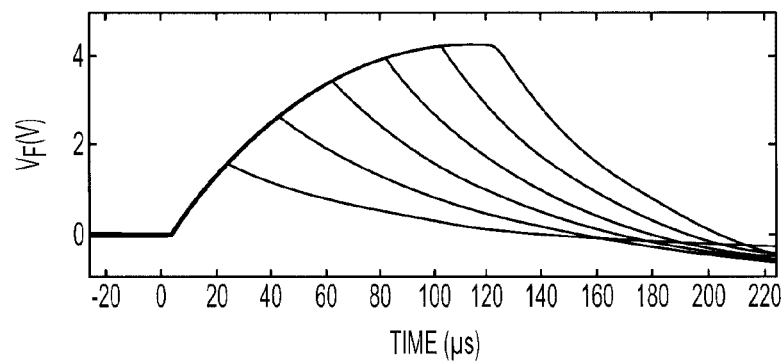
FIG. 15C shows illustrative waveforms of estimated neuronal membrane voltage change for different pulse widths induced with the controllable pulse parameter transcranial magnetic stimulation circuit of FIG. 14.

Referring to FIGS. 15A-C, illustrative waveforms of measured capacitor C5 voltage (FIG. 15A), search coil voltage $V_S$ (proportional to the induced electric field, FIG. 15B), and the estimated shape of the neuronal membrane voltage (VF) (FIG. 15C), which is determined by filtering the search coil voltage $V_S$ through a low-pass filter, are shown. The waveforms show six different pulse widths (i.e., 20, 40, 60, 80, 100, and 120 μs). It can be seen in FIG. 15B that the induced pulses, which are proportional to the electric field, have approximately rectangular shape, especially for brief pulses (e.g., 20 μs pulse).

As expected, overshoot and high-frequency ringing are present on the capacitor C5 voltage (FIG. 15A) and search coil voltage (proportional to the electric field, FIG. 15B) during switch Q1 turn-off, due to stray inductance. However, these transients are suppressed to a safe level by the snubber circuits. In particular, the capacitor voltage overshoot does not exceed 7% of the initial capacitor voltage, and the voltage across the switch Q1 never exceeds approximately twice the initial capacitor voltage, and is thus well below the 4,500 V rating of the IGBT (Q1). These results indicate the feasibility of high coil current commutation through appropriate choice of semiconductor switches, switch gating, snubber design, and minimization of stray inductance.

The above described cTMS implementation can be used to compare the intrinsic efficiency of rectangular unipolar electric field pulses versus conventional unipolar cosine pulses. In order to emulate conventional monophasic magnetic field pulses, the cTMS implementation was reconfigured to use a smaller capacitor and switch Q1 was kept on until the coil current decayed to zero. The comparison of rectangular pulses used the same initial capacitor voltage, and the cTMS pulse width was adjusted to achieve the same estimated neuronal depolarization. The energy dissipation per pulse was calculated using the formula:

$$\Delta W_C = \left(1/2 \sum_{\substack{\text{sum of all} \\ \text{capacitors} \\ \text{before pulse}}} C_i(V_{Ci})^2\right) - \left(1/2 \sum_{\substack{\text{sum of all} \\ \text{capacitors} \\ \text{after pulse}}} C_i(V_{Ci})^2\right),$$

where $C_i$ refers to all capacitors in the stimulator power electronics, and where capacitor $C_i$ has voltage $V_{Ci}$.

Compared to conventional monophasic magnetic field pulses with rise times of 72 and 101 µs, the corresponding rectangular pulses dissipated 20 and 28% less energy, respectively. The cTMS circuit of FIG. 14 does not recycle pulse energy (pulse energy is dissipated in resistor R1 in FIG. 14), so this gain in efficiency comes solely from the rectangular pulse shape. With energy recycling, which is implemented in the circuit in FIG. 2 and FIG. 3, efficiency will be even higher, as discussed above.

The cTMS system disclosed herein enables an operator to adjust various pulse shape parameters (previously described in detail) of an electric field pulse induced in the brain of a patient. The values of these pulse shape parameters can be chosen based on which medical application is being implemented and/or a patient's physiological characteristics. Further, the capability to control pulse parameters enables a medical professional to study the contribution of pulse characteristics to observed physiological effects of an induced electric field pulse.

Additionally, the cTMS systems disclosed herein (see FIGS. 2 and 3) produce approximately rectangular induced electric field pulses, which are more energy efficient for neuronal stimulation than sinusoidal pulses produced by existing TMS systems, as previously described. Moreover, the cTMS systems depicted in FIGS. 2 and 3 also enable an operator to vary the degree of bidirectionality of the induced pulse over a continuous range from a predominantly unipolar to a bipolar electric field pulse.

In view of the effects of the TMS pulse characteristics on physiological responses, and the capability of cTMS systems disclosed herein to control the pulse parameters, the cTMS systems disclosed herein have the potential for enabling diverse clinical and research applications. For example, the cTMS systems can be used to determine strength-duration curves (i.e., the induced electric field pulse amplitude vs. the pulse width that produces threshold neuronal stimulation). Strength-duration curves can be used to estimate a neuronal membrane time constant, and can therefore be a useful tool for diagnosing and studying neurological disease. Strength-duration curves can also be used to optimize stimulation paradigms for different cortical regions, and activate selectively different neuronal types possessing different membrane time constants and responsivity to pulse shape characteristics. Thus, the capability to adjust the pulse shape in the cTMS system could enable optimization of the stimulus parameters for various applications.

TMS with briefer, high-amplitude pulses requires less energy delivered to the stimulating coil, thereby increasing efficiency and decreasing heating. Thus, TMS and rTMS with brief (e.g., 20-50 µs) rectangular pulses are more energy efficient.

Recent studies indicate that rTMS with predominately unipolar induced electric fields can yield more potent modulation of neuronal excitability compared to standard bidirectional rTMS.

See for example: M. Sommer, N. Lang, F. Tergau, and W. Paulus, "Neuronal tissue polarization induced by repetitive transcranial magnetic stimulation" Neuroreport, vol. 13, no. 6, pp. 809-11, 2002; A. Antal, T. Z. Kincses, M. A. Nitsche, O. Bartfai, I. Demmer, M. Sommer, and W. Paulus, "Pulse configuration-dependent effects of repetitive transcranial magnetic stimulation on visual perception," Neuroreport, vol. 13, no. 17, pp. 2229-33, 2002; T. Tings, N. Lang, F. Tergau, W. Paulus, and M. Sommer, "Orientation-specific fast rTMS maximizes corticospinal inhibition and facilitation," Exp Brain Res, vol. 164, no. 3, pp. 323-33, 2005; N. Arai, S. Okabe, T. Furubayashi, Y. Terao, K. Yuasa, and Y. Ugawa, "Comparison between short train, monophasic and biphasic repetitive transcranial magnetic stimulation (rTMS) of the human motor cortex," Clin Neurophysiol, vol. 116, no. 3, pp. 605-13, 2005; and J. L. Taylor and C. K. Loo, "Stimulus waveform influences the efficacy of repetitive transcranial magnetic stimulation," J Affect Disord, vol. 97, pp. 271-276, 2007.

The cTMS system circuit (see FIGS. 2 and 3) is intrinsically energy efficient since the coil transfers charge between two energy-storage capacitors, rather than dissipating it in a resistor, like the conventional monophasic TMS topology does. Further, the cTMS system (see FIGS. 2 and 3) can induce predominately unipolar electric fields with biphasic magnetic pulses having fast rise time and slow fall times, which require substantially less energy delivered to the coil. Thus, such cTMS enables high-frequency unidirectional rTMS, yielding potentially stronger neuromodulation effects that can be used for therapeutic purposes in neurological and psychiatric illness.

Variations, modifications, and other implementations of what is described herein may occur to those of ordinary skill in the art without departing from the spirit and scope of the disclosed subject matter. Further, the various features of the embodiments described herein also can be combined, rearranged, or separated without departing from the spirit and scope of the disclosed subject matter as defined by the following claims.

I claim:

1. A magnetic stimulation system for inducing approximately rectangular electric field pulses in a body organ, comprising:
   an electrical energy storage device comprising a first capacitor and a second capacitor coupled to charging means for being respectively charged positively and negatively by said charging means to respective operator-controlled voltages;
   a stimulating coil; and
   a switching means for electrically coupling said electrical energy storage device to said stimulating coil to produce current pulses in said stimulating coil which generates, in response to the current pulses, magnetic field pulses that can induce approximately rectangular electric field pulses in the body organ,
   wherein said switching means comprises a first semiconductor switch and a second semiconductor switch, the first and second capacitors being alternatingly electrically coupled to said stimulating coil by said first and second semiconductor switches, respectively.

2. The system of claim 1, wherein the magnetic field pulses induce positive and negative electric field pulses in the body organ, with at least the positive electric field pulses comprising the approximately rectangular electric field pulses.

3. The system of claim 2, wherein the induced positive and negative electric field pulses are bipolar pulses.

4. The system of claim 1, further comprising an operator-controlled apparatus that includes means for selectively adjusting a pulse width of the induced electric field pulses.

5. The system of claim 1, wherein the magnetic field pulses induce positive and negative electric field pulses in the body organ, and wherein the system further comprises an operator-controlled apparatus that includes means for selectively adjusting a degree of bidirectionality of the induced positive and negative electric field pulses.

6. A system for inducing approximately rectangular electric field pulses in a body organ, comprising:
   an electrical energy storage device;
   a stimulating coil;

a switching device electrically coupling said electrical energy storage device to said stimulating coil and configured to produce current pulses in said stimulating coil and, in response to said current pulses, magnetic field pulses capable of inducing electric field pulses in the body organ; and a user-controlled device configured to selectively adjust over a continuous range of values a plurality of parameters of the induced electric field pulses in the body organ and configured to independently control the parameters of the electric field pulses induced in the body organ;

wherein the electrical energy storage device includes a first electrical energy storage device and a second electrical energy storage device, and the switching device includes a first switching device and a second switching device, the first and second energy storage devices being alternatingly electrically coupled to said coil by respective said first and second switching devices.

7. The system of claim 6, wherein the parameters include pulse amplitude, pulse width, pulse repetition frequency, and degree of bidirectionality.

8. The system of claim 7, wherein the user-controlled device is configured to independently control at least two of the parameters.

9. The system of claim 6, wherein the first and second switching devices are adapted to switch between an ON state and an OFF state in response to timing pulses generated by the user-controlled device.

10. The system of claim 9, wherein the user-controlled device is configured to selectively adjust the width of the electrical field pulses induced in the body organ by independently adjusting a time interval in which the first switching device is in an ON state, and a time interval in which the second switching device is in an ON state.

11. The system of claim 10, wherein adjusting the width of the electrical field pulses induced in the body organ further includes adjusting a first and second phase of the induced electric field pulses independently of each other, the first and second phases having opposite polarity.

12. The system of claim 10, wherein the user-controlled device is configured to control the width of the electrical field pulses induced in the body organ by independently controlling the timing pulses sent to the first and second switching devices.

13. The system of claim 7, wherein the user-controlled device is configured to selectively adjust the degree of bidirectionality of the electrical field pulses induced in the body organ by adjusting a ratio of the voltage supplied to the first energy storage device and the voltage supplied to the second energy storage device.

14. The system of claim 13, wherein the user-controlled device is configured to control the degree of bidirectionality of the electrical field pulse induced in the body organ by independently selecting the voltage supplied to the first energy storage device and the voltage supplied to the second energy storage device.

15. The system of claim 14, wherein the first and second energy storage devices are capacitors.

16. The system of claim 15, wherein the system further comprises a charging device to charge the first capacitor to an independently selectable positive voltage and to charge the second capacitor to an independently selectable negative voltage, wherein the user-controlled device is configured to independently select the positive and negative voltages.

17. The system of claim 16, wherein the user-controlled device is configured the adjust the bidirectionality the electric field pulses so that the field pulses induced in the body organ can be varied from bipolar pulses to substantially unipolar pulses.

18. The system of claim 6, further comprising a detecting device to detect physiological effects induced in the body organ by the electric field pulses.

19. The system of claim 18, wherein the user-controlled device is configured to adjust and control the parameters based on the detected physiological effects in the body organ.

20. The system of claim 19, wherein the physiological effect detected is a voltage change on the neuronal membrane of the body organ.

21. The system of claim 6, wherein the first and second switching devices are semiconductor switching devices, each comprising one of an insulated gate bipolar transistor and a gate turn-off thyristor.

22. A system for inducing approximately rectangular electric field pulses in a body organ, comprising:

a first electrical energy storage device configured to be charged to an independently selectable positive voltage;

a second electrical storage device configured to be charged to an independently selectable negative voltage;

a stimulating coil;

a switching device electrically coupling said first energy storage device for a first period of time to produce current pulses with a positive rate of change in the stimulating coil and electrically coupling said second electrical energy storage device for a second period of time to said stimulating coil to produce current pulses with a negative rate of change in the stimulating coil, and configured to produce, in response to said current pulses, magnetic field pulses capable of inducing approximately rectangular electric field pulses in the body organ; and a user-controlled device configured to selectively adjust over a continuous range of values a plurality of parameters of the induced electric field pulses in the body organ and configured to independently control the parameters of the electric field pulses induced in the body organ, wherein the user-controlled device is further configured to independently select said positive and negative voltages, and wherein the voltages on the energy storage devices are not reversed during a pulse.

23. The system of claim 22, wherein the parameters include pulse amplitude, pulse width, pulse repetition frequency, and degree of bidirectionality.

24. The system of claim 23, wherein the user-controlled device is configured to independently control at least two of the parameters.

25. The system of claim 23, wherein the first and second electrical energy storage devices include capacitors and the switching device includes a first switching device and a second switching device, the first and second capacitors being alternatingly electrically coupled to said coil by said respective first and second switching devices.

26. The system of claim 25, wherein the first and second switching devices are adapted to switch between an ON state and an OFF state in response to timing pulses generated by the user-controlled device.

27. The system of claim 26, wherein the user-controlled device is configured to selectively adjust the width of the electrical field pulses induced in the body organ by independently adjusting a time interval in which the first switching device is in an ON state, and a time interval in which the second switching device is in an ON state.

28. The system of claim 27, wherein the user-controlled device is further configured to adjust a first phase and a second phase of the induced electric field pulses independently of each other, the first and second phases having opposite polarity.

29. The system of claim 27, wherein the user-controlled device is configured to control the width of the electrical field pulses induced in the body organ by independently controlling the timing pulses sent to the first and second switching devices.

30. The system of claim 29, wherein the user-controlled device is configured to selectively adjust the degree of bidirectionality of the electrical field pulses induced in the body organ by adjusting a ratio of the voltage supplied to the first energy storage member and the voltage supplied to the second energy storage member.

31. The system of claim 30, wherein the user-controlled device is configured to control the degree of bidirectionality of the electrical field pulse induced in the body organ by independently selecting the voltage supplied to the first energy storage member and the voltage supplied to the second energy storage member.

32. The system of claim 31, wherein the system further comprises a charging device to charge the first capacitor to an independently selectable positive voltage and to charge the second capacitor to an independently selectable negative voltage, wherein the user-controlled device is configured to independently select the positive and negative voltages.

33. The system of claim 32, wherein by adjusting the bidirectionality the electric field pulses, the field pulses induced in the body organ can be varied from bipolar pulses to substantially unipolar pulses.

34. The system of claim 22, further comprising a detecting device to detect physiological effects induced in the body organ by the electric field pulses.

35. The system of claim 34, wherein the user-controlled device is configured to adjust and control the parameters based on the detected physiological effects in the body organ.

36. The system of claim 35, wherein the physiological effect detected is a voltage change on the neuronal membrane of the body organ.

37. The system of claim 36, wherein the first and second switching devices are semiconductor switching devices, each comprising one of an insulated gate bipolar transistor and a gate turn-off thyristor.

38. A magnetic stimulation system for inducing approximately rectangular electric field pulses in a body organ, comprising:
a first electrical energy storage device configured to be charged to an independently selectable positive voltage;
a second electrical storage device configured to be charged to an independently selectable negative voltage;
a stimulating coil;
a switching device electrically coupling said first energy storage device for a first period of time to produce current pulses with a positive rate of change in the stimulating coil and electrically coupling said second electrical energy storage device for a second period of time to said stimulating coil to produce current pulses with a negative rate of change in the stimulating coil, and configured to produce, in response to said current pulses, magnetic field pulses capable of inducing approximately rectangular electric field pulses in the body organ; and
a protecting device electrically connected to the simulation coil to control potential voltage overshoots in the system,
wherein, the first and second electrical energy storage devices and the switching device are positioned relative to each other and are interconnected in such a way as to minimize stray inductance in the system.

39. The system of claim 38, wherein the protecting device is a snubber circuit.

40. The system of claim 39, wherein the snubber circuit is electrically connected in parallel with the first and second energy storage devices.

41. The system of claim 38, further comprising a user-controlled device configured to selectively adjust over a continuous range of values a plurality of parameters of the induced electric field pulses in the body organ and configured to independently control the parameters of the electric field pulses induced in the body organ.

42. The system of claim 41, wherein the user-controlled device is further configured to independently select said positive and negative voltages.

43. The system of claim 41, wherein the parameters include pulse amplitude, pulse width, pulse repetition frequency, and degree of bidirectionality.

44. The system of claim 43, wherein the first and second switching devices are adapted to switch between an ON state and an OFF state in response to timing pulses generated by the user-controlled device and the user-controlled device is configured to selectively adjust the width of the electrical field pulses induced in the body organ by independently adjusting a time interval in which the first switching device is in an ON state, and a time interval in which the second switching device is in an ON state.

45. The system of claim 44, wherein the user-controlled device is further configured to adjust a first and second phase of the induced electric field pulses independently of each other, the first and second phases having opposite polarity.

46. The system of claim 44, wherein the user-controlled device is configured to control the width of the electrical field pulses induced in the body organ by independently controlling the timing pulses sent to the first and second switching devices.

47. The system of claim 43, wherein the user-controlled device is configured to selectively adjust the degree of bidirectionality of the electrical field pulses induced in the body organ by adjusting a ratio of the voltage supplied to the first energy storage device and the voltage supplied to the second energy storage device, and the user-controlled device is configured to control the degree of bidirectionality of the electrical field pulse induced in the body organ by independently selecting the voltage supplied to the first energy storage device and the voltage supplied to the second energy storage device.

* * * * *